United States Patent
Andino et al.

(10) Patent No.: US 10,188,550 B2
(45) Date of Patent: Jan. 29, 2019

(54) APPARATUS AND METHODS FOR DRUG DELIVERY USING MULTIPLE RESERVOIRS

(71) Applicant: Clearside Biomedical, Inc., Alpharetta, GA (US)

(72) Inventors: Rafael Victor Andino, Grayson, GA (US); Samirkumar R. Patel, Atlanta, GA (US); Vladimir Zarnitsyn, Atlanta, GA (US); Christopher John Brooks, Glen Cove, NY (US)

(73) Assignee: CLEARSIDE BIOMEDICAL, INC., Alpharetta, GA (US)

( * ) Notice: Subject to any disclaimer, the term of this patent is extended or adjusted under 35 U.S.C. 154(b) by 0 days.

(21) Appl. No.: 14/894,161

(22) PCT Filed: May 30, 2014

(86) PCT No.: PCT/US2014/040254
§ 371 (c)(1),
(2) Date: Nov. 25, 2015

(87) PCT Pub. No.: WO2014/197317
PCT Pub. Date: Dec. 11, 2014

(65) Prior Publication Data
US 2016/0106584 A1    Apr. 21, 2016

Related U.S. Application Data

(60) Provisional application No. 61/830,324, filed on Jun. 3, 2013.

(51) Int. Cl.
*A61F 9/00*     (2006.01)
*A61M 5/19*    (2006.01)
(Continued)

(52) U.S. Cl.
CPC .............. *A61F 9/0017* (2013.01); *A61M 5/19* (2013.01); *A61J 1/2093* (2013.01); *A61M 5/284* (2013.01); *A61M 2005/31598* (2013.01)

(58) Field of Classification Search
CPC .... A61M 2005/31598; A61M 5/51596; A61M 5/19; A61M 5/31501; A61M 5/31535
(Continued)

(56) References Cited

U.S. PATENT DOCUMENTS 2,187,259 A    1/1940   Barnhart
2,841,145 A    7/1958   Epps
(Continued)

FOREIGN PATENT DOCUMENTS

CA    2639322           3/2009
CN    1229679 A         9/1999
(Continued)

OTHER PUBLICATIONS

Extended Search Report for European Application No. 13833318.2, dated Apr. 1, 2016.
(Continued)

*Primary Examiner* — Nathan R Price
*Assistant Examiner* — John A Doubrava
(74) *Attorney, Agent, or Firm* — Cooley LLP

(57) ABSTRACT

A cartridge, including a first member that defines an inner volume and a second member disposed therein, is disposed in a housing. A first reservoir is disposed in the inner volume in a position distal to the second member. The first member is partially disposed in a second reservoir, defined by the housing. The second member is configured to be moved from a first position, in which the first reservoir contains a drug and the second reservoir is fluidically isolated from the inner volume, toward a second position, in which the first reservoir and the second reservoir are in fluid communica- (Continued)

tion with the inner volume, such that the second reservoir receives a volume of the drug from the first reservoir. The first member and the second member are collectively moved relative to the second reservoir to expel the volume of the drug from the second reservoir.

30 Claims, 13 Drawing Sheets

(51) Int. Cl.
A61J 1/20 (2006.01)
A61M 5/315 (2006.01)
A61M 5/28 (2006.01)

(58) Field of Classification Search
USPC .................................................. 604/86–91
See application file for complete search history.

(56) References Cited

U.S. PATENT DOCUMENTS

| | | | |
|---|---|---|---|
| 2,939,459 A | | 6/1960 | Lazarte et al. |
| 3,376,999 A | * | 4/1968 | De Hart ............... A61M 5/19 222/135 |
| 3,477,432 A | | 11/1969 | Shaw |
| 3,739,947 A | * | 6/1973 | Baumann ............. A61M 5/284 206/219 |
| 3,762,540 A | * | 10/1973 | Baumann ............. A61J 1/2093 206/219 |
| 3,788,320 A | | 1/1974 | Dye |
| 3,964,482 A | | 6/1976 | Gerstel et al. |
| 4,226,328 A | | 10/1980 | Beddow |
| 4,377,897 A | | 3/1983 | Eichenbaum et al. |
| 4,383,530 A | | 5/1983 | Bruno |
| 4,417,887 A | | 11/1983 | Koshi |
| 4,501,363 A | | 2/1985 | Isbey, Jr. |
| 4,564,016 A | | 1/1986 | Maurice et al. |
| 4,601,708 A | | 7/1986 | Jordan |
| 4,615,331 A | | 10/1986 | Kramann |
| 4,689,040 A | | 8/1987 | Thompson |
| 4,708,147 A | | 11/1987 | Haaga |
| 4,717,383 A | | 1/1988 | Phillips et al. |
| 4,736,850 A | | 4/1988 | Bowman et al. |
| 4,755,169 A | | 7/1988 | Sarnoff et al. |
| 4,795,432 A | | 1/1989 | Karczmer |
| 4,804,371 A | | 2/1989 | Vaillancourt |
| 4,826,490 A | | 5/1989 | Byrne et al. |
| 4,826,871 A | | 5/1989 | Gressel et al. |
| 4,889,529 A | | 12/1989 | Haindl |
| 4,941,874 A | | 7/1990 | Sandow et al. |
| 4,966,773 A | | 10/1990 | Gressel et al. |
| 5,015,240 A | | 5/1991 | Soproni et al. |
| 5,024,662 A | | 6/1991 | Menes et al. |
| 5,066,276 A | | 11/1991 | Wang |
| 5,098,389 A | | 3/1992 | Cappucci |
| 5,137,447 A | | 8/1992 | Hunter |
| 5,172,807 A | | 12/1992 | Dragan et al. |
| 5,181,909 A | * | 1/1993 | McFarlane ........... A61M 5/315 604/191 |
| 5,273,530 A | | 12/1993 | del Cerro et al. |
| 5,279,564 A | | 1/1994 | Taylor |
| 5,295,972 A | | 3/1994 | Mischenko |
| 5,300,084 A | | 4/1994 | Johnson |
| 5,312,361 A | | 5/1994 | Zadini et al. |
| 5,364,373 A | | 11/1994 | Waskonig et al. |
| 5,364,374 A | | 11/1994 | Morrison et al. |
| 5,397,313 A | | 3/1995 | Gross |
| 5,409,457 A | | 4/1995 | Del Cerro et al. |
| 5,538,503 A | | 7/1996 | Henley et al. |
| 5,547,467 A | | 8/1996 | Pliquett et al. |
| 5,632,740 A | | 5/1997 | Koch et al. |
| 5,658,256 A | | 8/1997 | Shields |
| D383,049 S | | 9/1997 | Concari et al. |
| 5,667,491 A | | 9/1997 | Pliquett et al. |
| 5,681,825 A | | 10/1997 | Lindqvist et al. |
| 5,779,668 A | | 7/1998 | Grabenkort |
| 5,788,679 A | | 8/1998 | Gravlee, Jr. |
| 5,792,099 A | | 8/1998 | DeCamp et al. |
| 5,817,075 A | | 10/1998 | Giungo |
| 5,911,223 A | | 6/1999 | Weaver et al. |
| 5,952,378 A | | 9/1999 | Stjernschantz et al. |
| 5,968,022 A | | 10/1999 | Saito |
| 6,059,111 A | | 5/2000 | Davilla et al. |
| 6,083,199 A | | 7/2000 | Thorley et al. |
| 6,143,329 A | | 11/2000 | Kim |
| 6,159,218 A | | 12/2000 | Aramant et al. |
| 6,280,470 B1 | | 8/2001 | Peyman |
| 6,299,603 B1 | | 10/2001 | Hecker et al. |
| 6,309,347 B1 | | 10/2001 | Takahashi et al. |
| 6,309,374 B1 | | 10/2001 | Hecker et al. |
| 6,319,225 B1 | | 11/2001 | Sugita et al. |
| 6,319,240 B1 | | 11/2001 | Beck |
| 6,334,856 B1 | | 1/2002 | Allen et al. |
| 6,378,526 B1 | | 4/2002 | Bowman et al. |
| 6,387,078 B1 | | 5/2002 | Gillespie, III |
| 6,397,849 B1 | | 6/2002 | Bowman et al. |
| 6,432,090 B1 | | 8/2002 | Brunel |
| 6,503,231 B1 | | 1/2003 | Prausnitz et al. |
| 6,524,581 B1 | | 2/2003 | Adamis |
| 6,530,904 B1 | | 3/2003 | Edwards et al. |
| 6,540,725 B1 | | 4/2003 | Ponzi |
| 6,551,299 B2 | | 4/2003 | Miyoshi et al. |
| 6,611,707 B1 | | 8/2003 | Prausnitz et al. |
| 6,622,864 B1 | | 9/2003 | Debbs et al. |
| 6,743,211 B1 | | 6/2004 | Prausnitz et al. |
| 6,773,916 B1 | | 8/2004 | Thiel et al. |
| D499,153 S | | 11/2004 | Kuo |
| 6,883,222 B2 | | 4/2005 | Landau |
| 6,918,889 B1 | | 7/2005 | Brunel |
| 6,929,623 B2 | | 8/2005 | Stone |
| 6,936,053 B1 | | 8/2005 | Weiss |
| 6,979,316 B1 | | 12/2005 | Rubin et al. |
| 7,025,774 B2 | | 4/2006 | Freeman et al. |
| 7,150,735 B2 | | 12/2006 | Hickle |
| 7,207,965 B2 | | 4/2007 | Simon |
| 7,207,980 B2 | | 4/2007 | Christian et al. |
| 7,211,062 B2 | | 5/2007 | Kwon |
| 7,214,212 B2 | | 5/2007 | Pommereau et al. |
| 7,226,439 B2 | | 6/2007 | Prausnitz et al. |
| 7,316,676 B2 | | 1/2008 | Peyman et al. |
| 7,425,207 B2 | | 9/2008 | Miller et al. |
| 7,435,237 B2 | * | 10/2008 | Tan ..................... A61M 5/19 604/187 |
| 7,468,057 B2 | | 12/2008 | Ponzi |
| D590,690 S | | 4/2009 | Bertini |
| D598,543 S | | 8/2009 | Vogel et al. |
| 7,569,035 B1 | | 8/2009 | Wilmot et al. |
| 7,615,041 B2 | | 11/2009 | Sullivan et al. |
| 7,648,482 B2 | | 1/2010 | Edwards et al. |
| 7,678,077 B2 | | 3/2010 | Harris et al. |
| 7,678,078 B1 | | 3/2010 | Peyman et al. |
| 7,722,581 B2 | | 5/2010 | Peyman |
| 7,914,803 B2 | | 3/2011 | Chowhan et al. |
| 7,918,814 B2 | | 4/2011 | Prausnitz et al. |
| 7,918,874 B2 | | 4/2011 | Siegal |
| 7,947,660 B2 | | 5/2011 | Clark et al. |
| 7,967,772 B2 | | 6/2011 | McKenzie et al. |
| 8,003,124 B2 | | 8/2011 | Varner et al. |
| 8,114,110 B2 | | 2/2012 | Bednarek et al. |
| 8,137,312 B2 | | 3/2012 | Sundar et al. |
| 8,172,830 B2 | | 5/2012 | Christian et al. |
| 8,173,617 B2 | | 5/2012 | Clark et al. |
| 8,192,408 B2 | | 6/2012 | Nazzaro et al. |
| 8,197,435 B2 | | 6/2012 | Prausnitz et al. |
| 8,197,443 B2 | | 6/2012 | Sundar et al. |
| 8,221,353 B2 | | 7/2012 | Cormier et al. |
| 8,235,967 B2 | | 8/2012 | Chevallier et al. |
| D667,111 S | | 9/2012 | Robinson |
| 8,287,494 B2 | | 10/2012 | Ma |
| D672,506 S | | 12/2012 | Szymanski |
| 8,323,227 B2 | | 12/2012 | Hamatake et al. |
| 8,328,772 B2 | | 12/2012 | Kinast et al. |
| 8,337,421 B2 | | 12/2012 | Freeman et al. |

(56) References Cited

U.S. PATENT DOCUMENTS

| | | |
|---|---|---|
| 8,337,509 B2 | 12/2012 | Schieber et al. |
| 8,348,924 B2 | 1/2013 | Christian et al. |
| 8,430,862 B2 | 4/2013 | Peyman et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,770,361 B2 | 9/2017 | Andino et al. |
| 9,931,330 B2 | 4/2018 | Zarnitsyn et al. |
| 9,937,075 B2 | 4/2018 | Andino et al. |
| 9,956,114 B2 | 5/2018 | Andino et al. |
| 2001/0008961 A1 | 7/2001 | Hecker et al. |
| 2001/0051798 A1 | 12/2001 | Hochman |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0112981 A1 | 8/2002 | Cooper et al. |
| 2002/0156413 A1 | 10/2002 | Williams et al. |
| 2003/0009113 A1 | 1/2003 | Olson |
| 2003/0083645 A1 | 5/2003 | Angel et al. |
| 2003/0139729 A1 | 7/2003 | Stegmann et al. |
| 2003/0171722 A1 | 9/2003 | Paques et al. |
| 2003/0233070 A1 | 12/2003 | De La Serna et al. |
| 2004/0106904 A1 | 6/2004 | Gonnelli et al. |
| 2004/0122359 A1* | 6/2004 | Wenz ............ A61M 5/31511 604/82 |
| 2004/0141925 A1 | 7/2004 | Bosch et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0171507 A1 | 8/2005 | Christian et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0281862 A1 | 12/2005 | Karakelle et al. |
| 2006/0013859 A1 | 1/2006 | Yamada et al. |
| 2006/0036318 A1 | 2/2006 | Foulkes |
| 2006/0084942 A1 | 4/2006 | Kim et al. |
| 2006/0086689 A1 | 4/2006 | Raju |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093877 A1 | 4/2007 | Beecham et al. |
| 2007/0178197 A1 | 8/2007 | Larue et al. |
| 2007/0202186 A1 | 8/2007 | Yamamoto et al. |
| 2007/0225654 A1 | 9/2007 | Hess et al. |
| 2007/0233037 A1 | 10/2007 | Gifford et al. |
| 2007/0260201 A1 | 11/2007 | Prausnitz et al. |
| 2007/0270768 A1 | 11/2007 | Dacquay et al. |
| 2007/0282405 A1 | 12/2007 | Wong et al. |
| 2007/0287985 A1 | 12/2007 | Estes et al. |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0071246 A1 | 3/2008 | Nazzaro et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0152694 A1 | 6/2008 | Lobl et al. |
| 2008/0177239 A1 | 7/2008 | Li et al. |
| 2008/0228127 A1 | 9/2008 | Burns et al. |
| 2008/0234625 A1 | 9/2008 | Dacquay et al. |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0088721 A1 | 4/2009 | Bizemont et al. |
| 2009/0105749 A1 | 4/2009 | De Juan et al. |
| 2009/0148527 A1 | 6/2009 | Robinson |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van emelen et al. |
| 2010/0010452 A1 | 1/2010 | Paques et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0312120 A1 | 12/2010 | Meier |
| 2011/0004265 A1 | 1/2011 | Wenger et al. |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0282298 A1 | 11/2011 | Agian et al. |
| 2011/0306923 A1 | 12/2011 | Roy |
| 2012/0004245 A1 | 1/2012 | May et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0083727 A1 | 4/2012 | Barnett |

(56) References Cited

U.S. PATENT DOCUMENTS

| | | |
|---|---|---|
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0041265 A1 | 2/2013 | Sostek et al. |
| 2013/0060202 A1 | 3/2013 | Thorley et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0218102 A1 | 8/2013 | Iwase et al. |
| 2013/0218269 A1 | 8/2013 | Schachar et al. |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0012226 A1 | 1/2014 | Hochman |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0094752 A1 | 4/2014 | Hiles |
| 2014/0114243 A1 | 4/2014 | Smith et al. |
| 2014/0135716 A1 | 5/2014 | Clarke et al. |
| 2014/0194834 A1 | 7/2014 | Passaglia et al. |
| 2014/0200518 A1 | 7/2014 | Ekman et al. |
| 2014/0224688 A1 | 8/2014 | Slemmen et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0276482 A1 | 9/2014 | Astafieva et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0129456 A1 | 5/2015 | Miller et al. |
| 2015/0133415 A1 | 5/2015 | Whitcup |
| 2015/0209180 A1 | 7/2015 | Prausnitz et al. |
| 2015/0258120 A1 | 9/2015 | Zarnitsyn et al. |
| 2015/0320596 A1 | 11/2015 | Gifford, III et al. |
| 2016/0015895 A1 | 1/2016 | Blondino et al. |
| 2016/0193080 A1 | 7/2016 | Hammack et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2017/0095369 A1 | 4/2017 | Andino et al. |
| 2017/0224435 A1 | 8/2017 | Godfrey et al. |
| 2017/0224534 A1 | 8/2017 | Andino et al. |
| 2017/0290702 A1 | 10/2017 | Yamamoto et al. |
| 2017/0333416 A1 | 11/2017 | Zarnitsyn et al. |
| 2017/0340560 A1 | 11/2017 | Yamamoto et al. |
| 2018/0028358 A1 | 2/2018 | Andino et al. |
| 2018/0028516 A1 | 2/2018 | Zarnitsyn et al. |
| 2018/0042765 A1 | 2/2018 | Noronha et al. |
| 2018/0042767 A1 | 2/2018 | Andino et al. |
| 2018/0092897 A1 | 4/2018 | Zarnitsyn et al. |

FOREIGN PATENT DOCUMENTS

| | | |
|---|---|---|
| CN | 1604799 A | 4/2005 |
| CN | 101052434 A | 10/2007 |
| CN | 101351239 A | 1/2009 |
| CN | 201356711 Y | 12/2009 |
| CN | 101854891 A | 10/2010 |
| CN | 101959519 A | 1/2011 |
| CN | 103037802 A | 4/2013 |
| CN | 103209733 A | 7/2013 |
| CN | 103857431 A | 6/2014 |
| EA | 006961 | 6/2006 |
| EP | 1188456 A1 | 3/2002 |
| EP | 2193821 | 6/2010 |
| EP | 2307055 | 4/2011 |
| JP | 2009-183441 | 8/2009 |
| JP | 2009-531298 | 9/2009 |
| RU | 2344767 | 1/2009 |
| RU | 2353393 | 4/2009 |
| RU | 2428956 | 9/2011 |
| WO | WO 92/20389 | 11/1992 |
| WO | WO 2000/007530 | 2/2000 |
| WO | WO 2000/007565 | 2/2000 |
| WO | WO 2001/041685 | 6/2001 |
| WO | WO 2002/058769 | 8/2002 |
| WO | WO 2003/002094 | 1/2003 |
| WO | WO 2003/024507 | 3/2003 |
| WO | WO 2003/039633 | 5/2003 |
| WO | WO 2005/011741 | 2/2005 |
| WO | WO 2005/069831 | 8/2005 |
| WO | WO 2005/072701 | 8/2005 |
| WO | WO 2005/107845 | 11/2005 |
| WO | WO 2006/004595 | 1/2006 |
| WO | WO 2006/058189 | 6/2006 |
| WO | WO 2006/128034 | 11/2006 |
| WO | WO 2006/138719 | 12/2006 |
| WO | WO 2007/100745 | 9/2007 |
| WO | WO 2007/131050 | 11/2007 |
| WO | WO 2007/150018 | 12/2007 |
| WO | WO 2009/067325 | 5/2009 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/123722 | 10/2011 |
| WO | WO 2011/139713 | 11/2011 |
| WO | WO 2012/019136 | 2/2012 |
| WO | WO 2012/051575 | 4/2012 |
| WO | WO 2012/125869 | 9/2012 |
| WO | WO 2012/162459 | 11/2012 |
| WO | WO 2013/050236 | 4/2013 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/074823 | 5/2014 |
| WO | WO 2014/179698 | 11/2014 |
| WO | WO 2014/197317 | 12/2014 |
| WO | WO 2015/015467 | 2/2015 |
| WO | WO 2015/195842 | 12/2015 |
| WO | WO 2015/196085 | 12/2015 |
| WO | WO 2016/042162 | 3/2016 |

(56) References Cited

FOREIGN PATENT DOCUMENTS

| WO | WO 2016/042163 | 3/2016 |
|---|---|---|
| WO | WO 2017/120600 | 7/2017 |
| WO | WO 2017/120601 | 7/2017 |
| WO | WO 2017/139375 | 8/2017 |
| WO | WO 2017/190142 | 11/2017 |
| WO | WO 2017/192565 | 11/2017 |

OTHER PUBLICATIONS

Office Action for U.S. Appl. No. 14/424,685, dated Jun. 10, 2016, 10 pages.
Final Office Action for U.S. Appl. No. 14/424,685, dated Dec. 12, 2016.
Supplementary Partial European Search Report for European Application No. 13853777, dated Jul. 4, 2016, 6 pages.
Search Report and Written Opinion for Singapore Application No. 11201503637S, dated Jun. 23, 2016, 9 pages.
Office Action for U.S. Appl. No. 14/441,151, dated Sep. 9, 2016, 18 pages.
Office Action for U.S. Appl. No. 15/001,610, dated Sep. 8, 2016, 12 pages.
Office Action for U.S. Appl. No. 15/086,485, dated Jul. 28, 2016, 9 pages.
Supplementary European Search Report for European Application No. 14808034.4, dated Jan. 23, 2017, 7 pages.
Office Action for Eurasian Application No. 201592109, dated Apr. 1, 2016, 4 pages.
Extended Search Report for European Application No. 14791646.4, dated Nov. 21, 2016.
Search Report and Written Opinion for Singapore Application No. 11201509051V, dated Nov. 2, 2016, 6 pages.
Examination Report for Singapore Application No. 11201509051V, dated Feb. 1, 2017, 4 pages.
Office Action for U.S. Appl. No. 14/268,687, dated May 19, 2016, 6 pages.
International Search Report and Written Opinion for International Application No. PCT/US2015/036299, dated Nov. 10, 2015, 11 pages.
Office Action for U.S. Appl. No. 15/383,582, dated May 5, 2017, 10 pages.
International Search Report and Written Opinion for International Application No. PCT/US2015/036715, dated Jan. 19, 2016, 9 pages.
Office Action for U.S. Appl. No. 11/709,941, dated Apr. 12, 2016, 25 pages.
Office Action for U.S. Appl. No. 11/709,941, dated Dec. 27, 2016.
Office Action for U.S. Appl. No. 13/842,218, dated Jul. 5, 2016, 11 pages.
First Office Action for Chinese Application No. 201180060268.9, dated Oct. 10, 2014.
Third Office Action for Chinese Application No. 201180060268.9, dated Feb. 5, 2016, 6 pages.
Examination Report for European Application No. 11776049.6, dated Oct. 25, 2016.
Office Action for Chinese Application No. 201510144330.2, dated Apr. 5, 2016.
Second Office Action for Chinese Application No. 201510144330.2, dated Dec. 20, 2016, 13 pages.
Office Action for U.S. Appl. No. 15/427,823, dated Apr. 20, 2017, 8 pages.
International Search Report and Written Opinion for International Application No. PCT/US2017/017014, dated Apr. 27, 2017, 13 pages.
Abbott Medical Optics (HEALON5@OVD on http://abbottmedicaloptics.com/products/cataract/ovds/healon5-viscoelastic (2004).
Dinning, W.J., "Steroids and the eye-indications and complications," Postgraduate Medical Journal, vol. 52, 1976, pp. 634-638.
Doncaster and Bassetlaw Hospitals, NHS Foundation Trust, "Intravitreal injection of triamcinolone," Jul. 2010, [Online], <URL: http://www.dbh.nhs.uk/Library/Patient_Information_Leaflets/WPR32110%20IIT%20No%20crops.pdf>, 2 pages.
Lee et al., "Thixotropic property in pharmaceutical formulations," Journal of Controlled Release (2009) 136:88-98.
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Patel, S. R. et al., "Targeted administration into the suprachoroidal spcae using a microneedle for drug delivery to the posterior segment of the eye," Investigative Ophthalmology & Visual Science, 53(8):4433-4441 (Jul. 2012).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
International Search Report and Written Opinion for PCT/US2014/040254, dated Oct. 31, 2014.
Office Action for U.S. Appl. No. 11/743,535, dated Aug. 19, 2010, 7 pages.
Office Action for U.S. Appl. No. 11/743,535, dated Dec. 29, 2009, 6 pages.
International Search Report and Written Opinion for International Application No. PCT/US2007/068055, dated Nov. 7, 2007, 13 pages.
Office Action for Russian Application No. 2012147341, dated Feb. 26, 2015, 8 pages.
Office Action for U.S. Appl. No. 12/767,768, dated Jun. 10, 2011, 5 pages.
International Search Report and Written Opinion for International Application No. PCT/US2011/033987, dated Feb. 14, 2012, 7 pages.
Office Action for U.S. Appl. No. 13/447,246, dated Oct. 28, 2013, 5 pages.
Office Action for U.S. Appl. No. 13/453,407, dated Mar. 20, 2013, 5 pages.
International Search Report and Written Opinion for International Application No. PCT/US2014/036590, dated Dec. 10, 2014, 10 pages.
Office Action for U.S. Appl. No. 14/523,243, dated Feb. 27, 2015, 14 pages.
Office Action for Canadian Application No. 162010, dated Aug. 25, 2015.
Office Action for Japanese Application No. 2013-534049, dated Sep. 1, 2015.
Anthem, Medical Policy, Suprachoroidal Injection of a Pharmacologic Agent, Nov. 14, 2013, Retrieved from the Internet: <URL: http://www.anthem.com/medicalpolicies/policies/mp_pw_b076412.htm>, 3 pages.
Beer, P. J. et al., "Photographic Evidence of Vitreous Wicks After Intravitreal Injections," Retina Today, 2(2):24-39 (Mar. 2007).
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Opthalmol Vis Sci., 51:E-Abstract 5330 (2010), 2 pages.
Careforde Healthcare, B Braun Glass Loss-Of-Resistance Syringes # 332155—5cc Glass Loss-Of-Resistance Syringe, Luer Lock Metal Tip, 10/cs, (2014), 2 pages.
Careforde Healthcare, B Braun Glass Loss-Of-Resistance Syringes # 332158—10cc Glass Loss-Of-Resistance Syringe, Luer Slip Metal Tip, 10/cs, [online], <http://careforde.com/b-braun-glass-loss-of-resistance-syringes-332158-10cc-glass-loss-of . . . > (2014), 2 pages.
Careforde Healthcare, B Braun Perifix Plastic Loss-Of-Resistance Syringes # 332152—8cc Plastic Luer Lock Loss-of-Resistance Syringe, 50/cs, [online], <http://careforde.com/b-braun-perifix-plastic-loss-of-resistance-syringes-332152-8cc-plasti . . . > (2014), 2 pages.
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).

(56) References Cited

OTHER PUBLICATIONS

Edwards, A. et al., "Fiber matrix model of sclera and corneal stroma for drug delivery to the eye," AIChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
"Epidural," Wikipedia [online], retrieved from the internet on Sep. 3, 2014, <URL: http:/en.wikipedia.org/wiki/Epidural>, 21 pages.
Feldkamp, L. A. et al., "Practical cone-beam algorithm," J. Opt. Soc. Am. A, 1(6):612-619 (1984).
Geroski, D. H. et al., "Drug delivery for posterior segment eye disease," Invest. Ophthalmol. Vis. Sci., 41(5):961-964 (2000).
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Hoagan et al., Chapter Eight, Choroid, In Histology of the Human Eye, 9 pages, (1971).
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Measurement and Prediction of Lateral Diffusion within Human Sclera," Investigative Ophthalmology & Visual Science, 47(7):3011-3016 (2006).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Lee, S-B et al., "Drug delivery through the sclera: effects of thickness, hydration and sustained release systems," Experimental Eye Research, 78:599-607 (2004).
Lindfield, D. et al., "Suprachoroidal Devices in Glaucoma. The Past, Present, and Future of Surgery for Suprachoroidal Drainage," Cataract & Refractive Surgery Today [online], Oct. 2013, Retrieved from the Internet: <URL: http://bmctoday.net/crstodayeurope/2013/10/article.asp?f=suprachoroidal-devices-in-glau . . . >, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).
Norman, D., Epidural analgesia using loss of resistance with air versus saline: Does it make a difference? Should we reevaluate our practice?, AANA Journal, 71(6):449-453 (Dec. 2003).
Olsen, T. W. et al., "Cannulation of the Suprachoroidal Space: A Novel Drug Delivery Methodology to the Posterior Segment," American J. Opthamology, 142(5):777-787 (2006).
Olsen, T., "Drug Delivery to the Suprachoroidal Space Shows Promise," Retina Today, pp. 36-39 (Mar./Apr. 2007).
Patel, S. et al., "Suprachoroidal Drug Delivery Using Microneedles," Invest. Ophthalmol. Vis. Sci., 49:E-Abstract 5006 (2008), 2 pages.
Patel, S. et al., "Drug Binding to Sclera," Invest Ophthalmol Vis Sci., 50:E-Abstract 5968 (2009), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Penkov, M. A. et al., "A ten-year experience with usage of the method of supra-choroidal administration of medicinal substances," Oftalmol. Zh., 35(5):281-285 (1980).
Prausnitz, M. R. et al., "Permeability of cornea, sclera and conjunctiva: A literature analysis for drug delivery to the eye," Journal of Pharmaceutical Sciences, 87(12):1479-1488 (1998).
Prausnitz, M. R. et al., "Measurement and prediction of transient transport across sclera for drug delivery to the eye," Industrial and Engineering Chemistry Research, 37(8):2903-2907 (1998).
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Shuler, R. K. et al., "Scleral Permeability of a Small, Single-Stranded Oligonucleotide," Journal of Ocular Pharmacology and Therapeutics, 20(2):159-168 (2004) (Abstract).
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
Office Action for Canadian Application No. 2797258, dated Nov. 21, 2016, 3 pages.
Examination Report No. 1 for Australian Application No. 2015230874, dated Jul. 28, 2017, 11 pages.
Office Action for Japanese Application No. 2016-068174, dated Mar. 1, 2017, 8 pages.
Office Action for U.S. Appl. No. 14/136,657, dated Dec. 16, 2016, 7 pages.
Office Action for European Application No. 14808034.4, dated Nov. 8, 2017, 4 pages.
Office Action for European Application No. 14791646.4, dated Dec. 4, 2017, 5 pages.
Extended European Search Report for European Application No. 15808944.1, dated Jan. 19, 2018, 14 pages.
Partial Supplementary European Search Report for European Application No. 15810459.6, dated Dec. 22, 2017, 13 pages.
Summons to Attend Oral Proceedings Pursuant to Rule 115(1) EPC for European Application No. 07751620.1, dated Jun. 13, 2017, 8 pages.
Office Action for U.S. Appl. No. 11/709,941, dated Jan. 16, 2018, 32 pages.
Third Office Action for Chinese Application No. 201510144330.2, dated Jun. 28, 2017, 3 pages.
Office Action for U.S. Appl. No. 14/821,310, dated Jul. 14, 2017, 11 pages.
First Office Action for Chinese Application No. 201610805842.3, dated Jul. 21, 2017, 4 pages.
Office Action for U.S. Appl. No. 15/427,823, dated Sep. 27, 2017, 7 pages.
International Search Report and Written Opinion for International Application No. PCT/US2017/012755, dated Apr. 12, 2017, 8 pages.
International Search Report and Written Opinion for International Application No. PCT/US2017/012757, dated Apr. 12, 2017, 11 pages.
International Search Report and Written Opinion for International Application No. PCT/US2017/030609, dated Oct. 6, 2017, 12 pages.
International Search Report and Written Opinion for International Application No. PCT/US2017/030439, dated Aug. 1, 2017, 12 pages.
International Search Report and Written Opinion for International Application No. PCT/US2017/046553, dated Dec. 13, 2017, 14 pages.
Brown, D. M., "Aflibercept for Treatment of Diabetic Macular Edema," Retina Today, Jul./Aug. 2011, pp. 59-60.
Cho, S. W. et al., "Drug delivery to the suprachoroidal space," Chap. 12 in: Ocular Drug Delivery Systems: Barriers and Application of Nanoparticulate Systems, Thassu, D. et al. (eds.), CRC Press, pp. 235-258 (2012).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).

(56) References Cited

OTHER PUBLICATIONS

Patel, S. R. et al., "Suprachoroidal drug delivery to the back of the eye using hollow microneedles," Pharmaceutical Research, 28(1):166-176 (2011). Published online: Sep. 21, 2010.

* cited by examiner

APPARATUS AND METHODS FOR DRUG DELIVERY USING MULTIPLE RESERVOIRS

CROSS-REFERENCE TO RELATED APPLICATIONS

This application claims priority under 35 U.S.C.§ 371 to, and is a U.S. national phase application of, International Application No. PCT/US2014/040254, filed May 30, 2014, entitled "APPARATUS AND METHODS FOR DRUG DELIVERY USING MULTIPLE RESERVOIRS," which claims priority to and the benefit of U.S. Provisional Application Ser. No. 61/830,324, filed Jun. 3, 2013 entitled "Apparatus and Methods for Drug Delivery Using Multiple Reservoirs," both of which are incorporated herein by reference in their entireties.

BACKGROUND

The embodiments described herein relate generally to the field of ophthalmic therapies and more particularly to apparatus and methods fir delivering a drug to ocular tissue using multiple drug reservoirs.

Although needles have been used in transdermal and intraocular drug delivery, there remains a need for improved microneedle devices and methods, particularly for delivery of substances (e.g., drugs) into the posterior region of the eye. Many inflammatory and proliferative diseases in the posterior region (or other regions) of the eye require long-term pharmacological treatment. Examples of such diseases include macular degeneration, diabetic retinopathy, and uveitis. It is often difficult to deliver effective doses of a drug to the back of the eye using conventional delivery methods such as topical application, which has poor efficacy, and systemic administration, which often causes significant side effects. For example, while eye drops are useful in treating conditions affecting the exterior surface of the eye or tissues at the front of the eye, the eye drops are not significantly carried to the back of the eye, as may be required for the treatment of some of the retinal diseases listed above. Therefore, intraocular delivery of a drug is often desirable.

Some known intraocular delivery devices include a vial or reservoir that can store a substance prior to delivery into the eye. For example, in some known systems a drug can be disposed within an inner volume of a syringe (e.g., a reservoir) and the syringe can be coupled to a microneedle that is suitable for insertion into ocular tissue. In such configurations, however, the user's ability to control the volume of the drug dispensed can be limited.

Moreover, in such known systems, the drug disposed within the syringe can begin to separate during storage which can lead to reduced efficacy of the drug. Although, some known injection devices include multiple chambers and/or multiple reservoirs that allow for mixing or agitating of the drug prior to injection, such known injection devices are generally not configured to deliver drugs into the eye. For example, in such devices, the mechanism for transferring the drug from a first chamber to a second chamber can be complex, which can lead to a loss of accuracy in controlling the dosage delivered, an increase in cost of the device and the like. In some instances, one or more of the chambers included in such devices are disposed within a casing or the like that can limit visualization of the drug within the syringe, which can lead to the drug not being properly mixed or agitated prior to injection and can also limit proper metering of the dosage to be delivered.

Thus, a need exists for improved apparatus and methods for storing and mixing a drug in two or more reservoirs prior to delivery into ocular tissue.

SUMMARY

Devices and methods described herein relate generally to intraocular treatment and more particularly to apparatus and methods for delivering a drug to ocular tissue using multiple drug reservoirs. In some embodiments, an apparatus includes a cartridge assembly that is movably disposed within a housing. The cartridge assembly includes a first member and a second member that collectively define a first reservoir. A portion of the first member and a portion of the housing collectively define a second reservoir. The second member is movable between a first position relative to the first member and a second position relative to the second member to move the cartridge assembly between a first configuration and a second configuration, respectively. The first reservoir is configured to contain a drug when the cartridge assembly is in the first configuration. When the cartridge assembly is moved from the first configuration to the second configuration, the drug flows within a flow path to be disposed within the second reservoir. The cartridge assembly is movable between a first position relative to the housing and a second position relative to the housing to expel the drug from the second reservoir.

DETAILED DESCRIPTION

Figure 1:
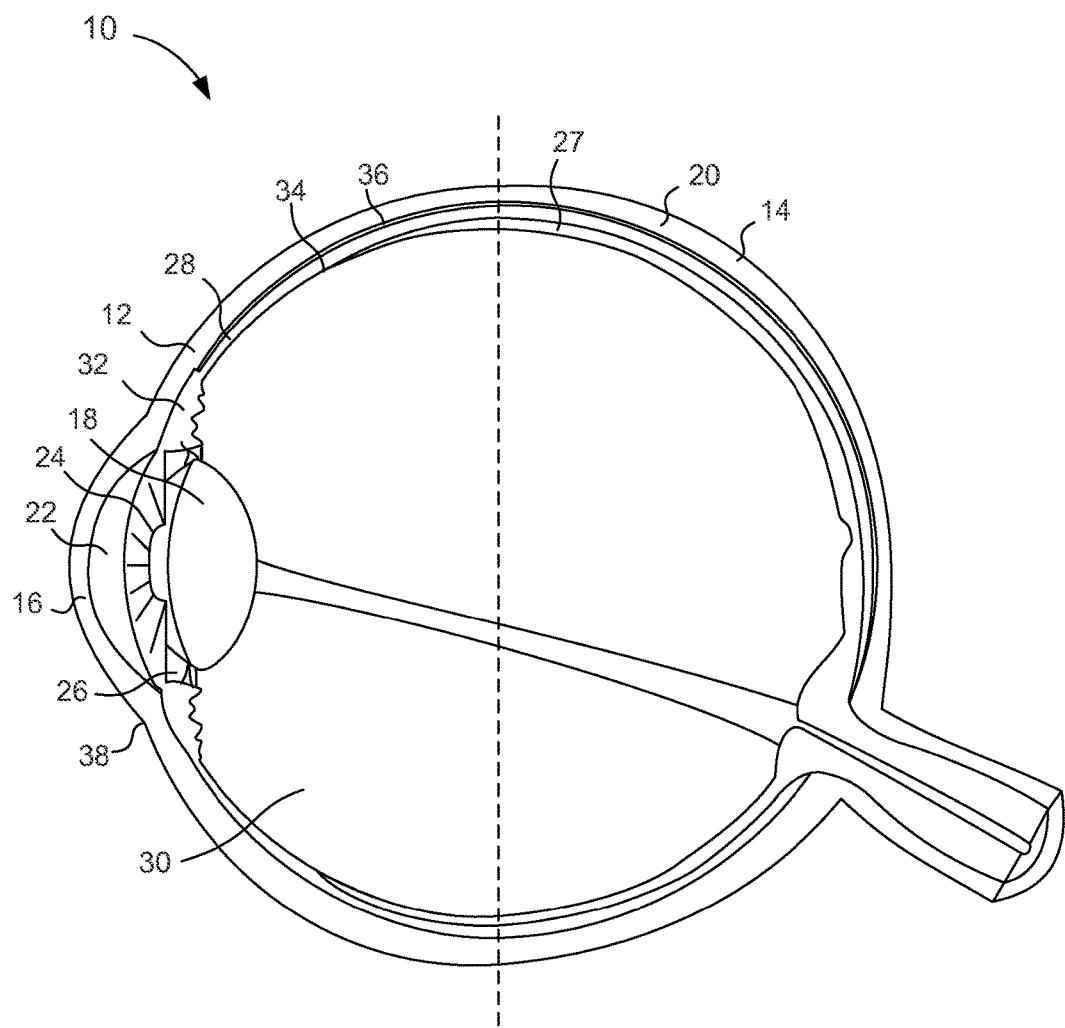
FIG. 1 is a cross-sectional view of an illustration of an eye.

The embodiments described herein relate to using multiple drug reservoirs to deliver a drug to, for example, the sclera of an eye to deliver the drug to, for example, a posterior region of the eye (e.g., via the suprachoroidal space). In some embodiments, the microneedles included in the embodiments described herein include a bevel, which, in comparison with standard bevels, allows for ease of penetration into the sclera and/or suprachoroidal space with minimal collateral damage. The narrow lumen (e.g., greater than or equal to 32 gauge, 34 gauge, 36 gauge, etc.) of the microneedle allows for suprachoroidal drug delivery while minimizing the diameter of the needle track caused by the insertion of the microneedle. The lumen and bevel aspect ratio of the microneedles described herein are distinct from standard 27 gauge and 30 gauge needles. For example, the microneedles included in the embodiments described herein can be any of those described in International Patent Application Publication No. WO2014/036009, entitled, "Apparatus and Methods for Drug Delivery Using Microneedles," filed on Aug. 27, 2013, the disclosure of which is incorporated by reference herein in its entirety (referred to henceforth as the "'009 PCT application").

In some embodiments, an apparatus includes a housing, a cartridge assembly, a first reservoir, and a second reservoir. At least a portion of the cartridge assembly is configured to be movably disposed in the housing. The cartridge assembly includes a first movable member and a second movable member. The first movable member defines an inner volume. At least a portion of the second movable member is movably disposed in the inner volume between a first position and a second position relative to the first movable member. The first reservoir is disposed within the inner volume in a distal position relative to the second movable member. The first reservoir is configured to contain a drug when the second movable member is in its first position relative to the first movable member and is configured to be placed in fluid communication with the inner volume when the second movable member is in its second position relative to the first movable member. The second reservoir is at least partially defined by the housing. A portion of the first movable member is movably disposed in the second reservoir such that when the second movable member is in its first position relative to the first movable member, the second reservoir is fluidically isolated from the inner volume. The second reservoir is configured to be placed in fluid communication with the inner volume when the second movable member is moved toward its second position relative to the first movable member to receive a volume of the drug from the first reservoir. The first movable member and the second movable member are collectively configured to be moved from a first position relative to the housing to a second position relative to the housing to expel the volume of the drug from the second reservoir.

In some embodiments, an apparatus includes a housing and a cartridge assembly. The housing has a distal end portion that defines a substantially rigid reservoir physically and fluidically coupled to a puncture member. The puncture member is configured to puncture ocular tissue of a patient. The cartridge assembly is configured to be movably disposed in the housing and includes a first movable member, a second movable member, and a deformable reservoir. At least a portion of the first movable member is configured to be disposed in the substantially rigid reservoir. The first movable member has an inner surface that forms a shoulder and that Minims an inner volume. At least a portion of the second movable member is movably disposed in the inner volume between a first position and a second position. The deformable reservoir is disposed within the inner volume between the shoulder and the second movable member. The shoulder is configured to selectively engage the deformable reservoir when the second movable member is moved relative to the first movable member to transition the deformable reservoir from a first configuration, in which a drug is contained within the deformable reservoir, and a second configuration, in which a volume of the drug is disposed substantially outside the deformable reservoir. The substantially rigid reservoir is configured to be fluidically isolated from the inner volume when the second movable member is in its first position and is configured to receive the volume of the drug from the inner volume when the second movable member is moved relative to the first movable member toward its second position. The first movable member of the cartridge assembly being movable relative to the housing from a first position to a second position to deliver the volume of the drug, via the puncture member, from the second reservoir to the ocular tissue.

In some embodiments, an apparatus includes a housing, a first movable member, a second movable member, a first reservoir, and a second reservoir. The housing includes a safety tab. A distal end portion of the housing is physically and fluidically coupled to a puncture member, which is configured to puncture ocular tissue. The first movable member is movably disposed in the housing and defines an inner volume. The safety tab is configured to engage the first movable member to selectively limit movement of the first movable member relative to the housing. The second movable member is at least partially disposed in the inner volume and is movable relative to the first movable member between a first position and a second position. The first reservoir is disposed within the inner volume and is configured to be transitioned between a first configuration, in which the first reservoir contains a drug, and a second configuration, in which a volume of the drug is disposed within the inner volume and substantially outside of the first reservoir, when the second movable member is moved from its first position to its second position, respectively. The second reservoir is at least partially defined by the housing. A portion of the first movable member is movably disposed in the second reservoir such that when the second movable member is in its first position, the second reservoir is fluidically isolated from the inner volume. The second reservoir is configured to be placed in fluid communication with the inner volume to receive the volume of the drug when the second movable member is moved toward its second position. The first movable member is configured to be disengaged from the safety tab and moved within the second reservoir from a first position to a second position to deliver the volume of the drug, via the puncture member, from the second reservoir to the ocular tissue.

In some embodiments, an apparatus includes a cartridge assembly that is movably disposed within a housing. The cartridge assembly includes a first member and a second member that collectively define a first reservoir. A portion of the first member and a portion of the housing collectively define a second reservoir. The second member is movable between a first position relative to the first member and a second position relative to the second member to move the cartridge assembly between a first configuration and a second configuration, respectively. The first reservoir is configured to contain a drug when the cartridge assembly is in the first configuration. When the cartridge assembly is moved from the first configuration to the second configuration, the drug flows within a flow path to be disposed within the second reservoir. The cartridge assembly is movable between a first position relative to the housing and a second position relative to the housing to expel the drug from the second reservoir.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a microneedle described herein first inserted inside the patient's body would be the distal end, while the opposite end of the microneedle (e.g., the end of the medical device being manipulated by or closest to the operator) would be the proximal end of the microneedle.

As used herein, a "set" can refer to multiple features or a singular feature with multiple parts. For example, when referring to set of walls, the set of walls can be considered as one wall with distinct portions, or the set of walls can be considered as multiple walls.

As used herein, the terms "about" and "approximately" generally mean plus or minus 10% of the value stated. For example, about 0.5 would include 0.45 and 0.55, about 10 would include 9 to 11, about 10000 would include 900 to 11000. Nominal differences in a. value can be attributed to, for example, manufacturing tolerances, measurement tolerances, or the like.

The embodiments and methods described herein can be used to treat various target tissues, such as, for example, tissue in the eye. For reference, FIG. 1 is a cross-sectional view of a human eye 10. While specific regions are identified, those skilled in the art will recognize that the proceeding identified regions do not solely constitute the eye 10, rather the identified regions are presented as a simplified example suitable for the discussion of the embodiments herein. The eye 10 includes both an anterior segment 12 (the portion of the eye in front of and including the lens) and a posterior segment 14 (the portion of the eye behind the lens). The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The cornea 16 and the sclera 20 collectively form a limbus 38 at the point at which they meet. The exposed portion of the sclera 2.0 on the anterior segment 12 of the eye is protected by a clear membrane referred to as the conjunctiva (not shown). Underlying the sclera 20 is the choroid 28 and the retina 27, collectively referred to as retinachoroidal tissue. A vitreous humour 30 (also referred to as the "vitreous") is disposed between a ciliary body 32 (including a ciliary muscle and a ciliary process) and the retina 27. The anterior portion of the retina 27 forms an ora serrata 34. The loose connective tissue, or potential space, between the choroid 28 and the sclera 20 is referred to as the suprachoroid.

As used herein, the term "suprachoroidal space," which is synonymous with suprachoroid, or suprachoroidia, describes the potential space in the region of the eye 10 disposed between the sclera 20 and choroid 28. (e.g., identified as the region 36 in FIG. 1). This region is primarily composed of closely packed layers of long pigmented processes derived from each of the two adjacent tissues; a space can develop in this region, however, as a result of fluid or other material buildup in the suprachoroidal space and the adjacent tissues. The suprachoroidal space is frequently expanded by fluid buildup because of a disease state in the eye or as a result of some trauma or surgical intervention. In some instances, the fluid buildup is intentionally created by the infusion of a drug formulation into the suprachoroid to create the suprachoroidal space 36 (which can be filled with drug formulation).

The dashed line in FIG. 1 represents the equator of the eye 10. In some instances, the insertion site of any of the microneedles and/or methods described herein is between the equator and the limbus 38 (i.e., in the anterior portion 12 of the eye 10). For example, in some instances, the insertion site can be between about two millimeters and about 10 millimeters (mm) posterior to the limbus 38. In other instances, the insertion site of the microneedle is at about the equator of the eye 10. In still other embodiments, the insertion site is posterior to the equator of the eye 10. In this manner, a drug formulation can be introduced (e.g., via a microneedle) into the suprachoroidal space 36 at the site of the insertion and can flow through the suprachoroidal space 36 away from the site of insertion during an infusion event (e.g., during injection).

Figure 2:
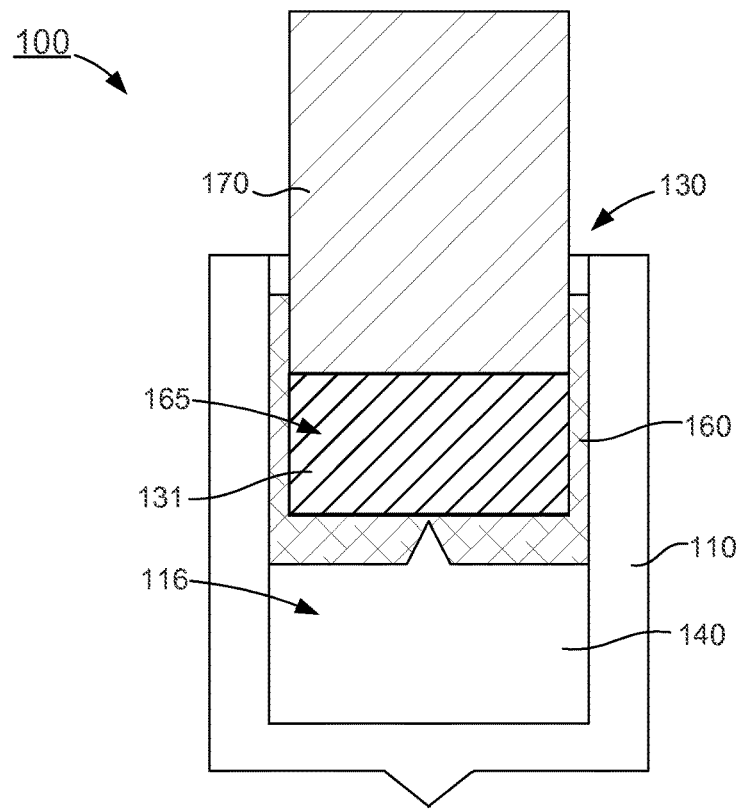
FIG. 2 is a schematic illustration of a delivery device according to an embodiment in a first configuration.
Figure 3:
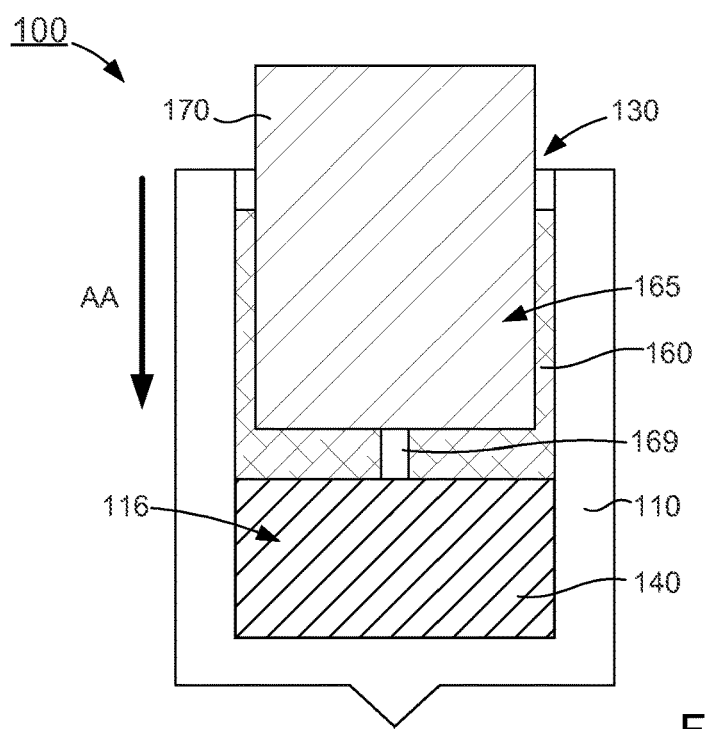
FIGS. 3 and 4 are schematic illustrations of the delivery device of FIG. 2, in a second configuration and a third configuration, respectively.
Figure 4:
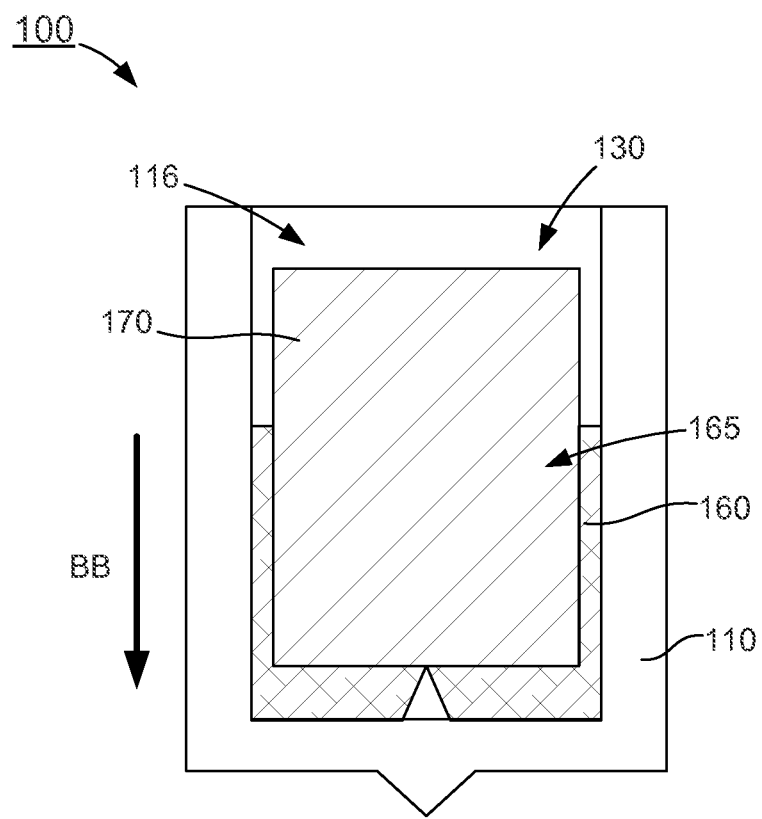

FIGS. 2-4 are schematic illustrations of a delivery device 100 according to an embodiment in a first, second, and third configuration, respectively. The delivery device 100 can be used, for example, to deliver a drug to ocular tissue such as the suprachoroidal space defined between the sclera and the choroid. The delivery device 100 includes housing 110 and a cartridge assembly 130 and is movable between a first configuration (FIG. 2), a second configuration (FIG. 3) and a third configuration (FIG. 4). The housing 110 can be any suitable shape, size, or configuration. For example, in some embodiments, the housing 110 can have a substantially annular and/or cylindrical shape that can define an inner volume 116. As described in further detail herein, the inner volume 116 can movably receive at least a portion of the cartridge assembly 130.

The cartridge assembly 130 includes a first movable member 160 and a second movable member 170. The cartridge assembly 130 can be moved between a first configuration (FIG. 2), a second configuration (FIG. 3), and a third configuration (FIG. 4) to move the delivery device 100 between its first configuration, its second configuration, and its third configuration, respectively. The first movable member 160 and the second movable member 170 are movably coupled such that the second movable member 170 can move with and/or relative to the first movable member 160. As shown, in some embodiments, the second movable member 170 can be disposed, at least partially, within the first movable member 160. For example, in some embodiments, the first movable member 160 can define a substantially annular and/or cylindrical shape such that at least a portion of the second movable member 170 can be movably disposed therein. More specifically, the first movable member 160 can define an inner volume 165 that movably receives the second movable member 170.

In some embodiments, the second movable member 170 can be a plunger or the like that can be moved between a first position and a second position (see e.g., FIGS. 2. and 3) relative to the first movable member 160. In some embodiments, at least a portion of an outer surface of the second movable member 170 can form a friction fit with an inner surface of the first movable member 160 that defines the inner volume 165. Similarly stated, at least a portion of the outer surface of the second movable member 170 can form a substantially fluidic seal with the inner surface of the first movable member 160 such that a portion of the inner volume 165 that is distal to the seal formed between the first movable member 160 and the second movable member 170 is fluidically isolated from a portion of the inner volume 165 that is proximal to the seal. In this manner, the first movable member 160 and the second movable member 170 can collectively house and/or collectively form a first reservoir 131 that can at least temporarily contain a drug. For example, as shown in FIG. 1, the first reservoir 131 can contain a drug formulation, a prophylactic agent, a therapeutic agent, a diagnostic agent, or any other suitable drug formulation such as, for example, those described herein.

The first movable member 160 includes an outer surface that can engage an inner surface of the housing 110 that defines the inner volume 116. More specifically, at least a portion of the first movable member 160 can include or can form a seal member that can form a friction fit with the inner surface of the housing 110 that defines the inner volume 116. In this manner, the portion of the first movable member 160 (e.g., a distal end portion) can be arranged to form a substantially fluidic seal between the seal member (not shown in FIGS. 2-4) and the inner surface of the housing 110. Similarly stated, at least a portion of the first movable member 160 can be and/or can form a plunger that is movably disposed within the inner volume 116 of the housing 110. Therefore, with the portion of the first movable member 160 forming a substantially fluidic seal with the inner surface of the housing 110, the first movable member 160 and the housing 110 can collectively house and/or can collectively form a second fluid reservoir 140 (see e.g., FIG. 2).

As described above, the first reservoir 131 can be configured to contain a drug while the delivery device 100 is in the first configuration (FIG. 2). In some instances, the delivery device 100 can be stored in the first configuration (e.g., with the drug stored in the first reservoir 131) prior to use. In other embodiments, the delivery device 100 can be stored hi a configuration in which the cartridge 130 (containing the drug) is spaced apart from and/or stored separately from the housing 110. In this manner, the cartridge 130 can be filled and/or stored in a different environment (e.g., filled in a clean room environment and stored in a refrigerated environment) from that in which the housing 110 is stored. In some instances, the delivery device 100 and/or the cartridge 130 can be stored for a length of time (e.g., 6 months or longer, one year or longer, two years or longer, three years or longer). In such instances, it can be desirable to nix and/or agitate the drug prior to delivery to, for example, ocular tissue. Such mixing and/or agitation can be accomplished according to any of the procedures and via any of the mechanisms described herein.

In use, an operator (e.g., a doctor, a physician, a technician, a nurse, an ophthalmologist, etc.) can manipulate the delivery device 100 to move the cartridge assembly 130 from its first configuration (FIG. 1) to its second configuration (FIG. 2). For example, in some embodiments, the user can exert a force on the second movable member 170 that is sufficient to move the second movable member 170 from a first position (e.g., a proximal position) relative to the first movable member 160 toward a second position relative to the first movable member 160 (e.g., a distal position), as indicated by the arrow AA in FIG. 3. In this manner, the cartridge 130 can be moved from its first configuration (e.g., FIG. 2) to its second configuration (e.g., FIG. 3). The movement of the cartridge assembly 130 from its first configuration to its second configuration corresponds to the movement of the delivery device 100 from the first configuration to the second configuration.

The movement of the second movable member 170 relative to the first movable member 160 can urge the drug to flow from the first reservoir 131 to the second reservoir 140. For example, in some embodiments, the force exerted by the user on the second movable member 170 can increase a pressure within the first reservoir 131 that is sufficient to urge the drug to flow within a flow path from the first reservoir 131 to the second reservoir 140. More specifically, in some embodiments, the first movable member 160 can include a valve 169 or the like (e.g., a one way valve, a frangible seal, or the like) that can be moved from a closed configuration (when the cartridge assembly 130 is in the first configuration, see FIG. 2) to an open configuration (when the cartridge assembly 130 is moved to the second configuration, see FIG. 3) when the pressure within the first reservoir 131 reaches a given threshold. In such embodiments, when the valve 169 is placed in the open configuration, the first movable member 160 can define at least a portion of the flow path within which the drug can flow from the first reservoir 131 to the second reservoir 140. Although shown and described as flowing through the valve 169 of the first movable member 160, in other embodiments, the flow path can be defined by any suitable structure or mechanism such as, for example, a channel defined by the housing 110 or the like. In some embodiments, such a channel can include a frangible seal that can be broken to expose a flow path. The flow of the drug from the first reservoir 131 to the second reservoir 140 can be such that the drug is mixed and/or agitated when the drug flows from the first reservoir 131 to the second reservoir 140. Thus, the drug can be reconstituted such that the particles of the drug are no longer separated.

As shown in FIG. 3, the second movable member 170 can be moved relative to the first movable member 160 to place a distal surface of the second movable member 170 in contact with a distal inner surface of the first movable member 160 such that substantially an entire volume of the drug flows within the flow path to the second reservoir 140. In other embodiments, the flow of the drug can be metered such that only a portion of the volume of the drug is disposed within the second reservoir 140. With the desired volume of the drug disposed in the second reservoir 140 the valve 169 can be moved from the open configuration to the closed configuration. For example, in some instances, the pressure within the first reservoir 131 can fall below a given threshold that allows the valve 169 to move from the open configuration to the closed configuration. In this manner, the drug can be metered in a manner to ensure accurate delivery of the drug to the target tissue.

With the desired amount of drug in the second reservoir 140, the cartridge assembly 130 can be moved from its second configuration to its third configuration. For example, in some embodiments, the user can exert a force on the first movable member 160 and/or the second movable member 170 that is sufficient to move the first movable member 160 from a first position relative to the housing 110 (e.g., a proximal position) to a second position relative to the housing 110 (e.g., a distal position), as indicated by the arrow BB in FIG. 4. Furthermore, the arrangement of the first movable member 160 and the second movable member 170 can be such that the second movable member 170 moves with the first movable member 160. Similarly stated, when the cartridge assembly 130 is moved within the housing 110 from its first configuration (FIG. 3) to its second configuration (FIG. 4), which moves the delivery device 100 from its second configuration to its third configuration, the first movable member 160 can be in a fixed position relative to the second movable member 170. Thus, the delivery device 100 can be moved from the second configuration to the third configuration, resulting in delivery of the drug, as discussed below.

The movement of the cartridge assembly 130 from the second configuration to the third configuration can urge the drug to flow from the second reservoir 140 such that the drug is expelled from the housing 110. For example, in some instances, the movement of the cartridge assembly 130 relative to the housing 110 can increase the pressure within the second reservoir a sufficient amount to urge the drug to flow from the second reservoir 140, By way of example, although not shown in FIGS. 2-4, the housing 110 can be coupled to and/or can include a puncture member that can define a lumen. The arrangement of the puncture member can be such that the lumen is in fluid communication with the second reservoir 140. In some embodiments, the puncture member can be, for example, a microneedle and/or a microcatheter that is suitable for insertion into ocular tissue. In this manner, a user can manipulate the delivery device 100 to insert the puncture member into the ocular tissue prior to the delivery device 100 being moved to the third configuration. Thus, with the puncture member disposed within the ocular tissue and with the lumen in fluid communication with the second reservoir 140, the drug can flow through the lumen to a target site such as, for example, the suprachoroidal space 36 of the eye 10 (FIG. 1).

In other embodiments, however, the delivery device 100 need not include a puncture member and/or a microneedle. For example, in some embodiments, the delivery device 100 can be a needle-less device.

Figure 5:
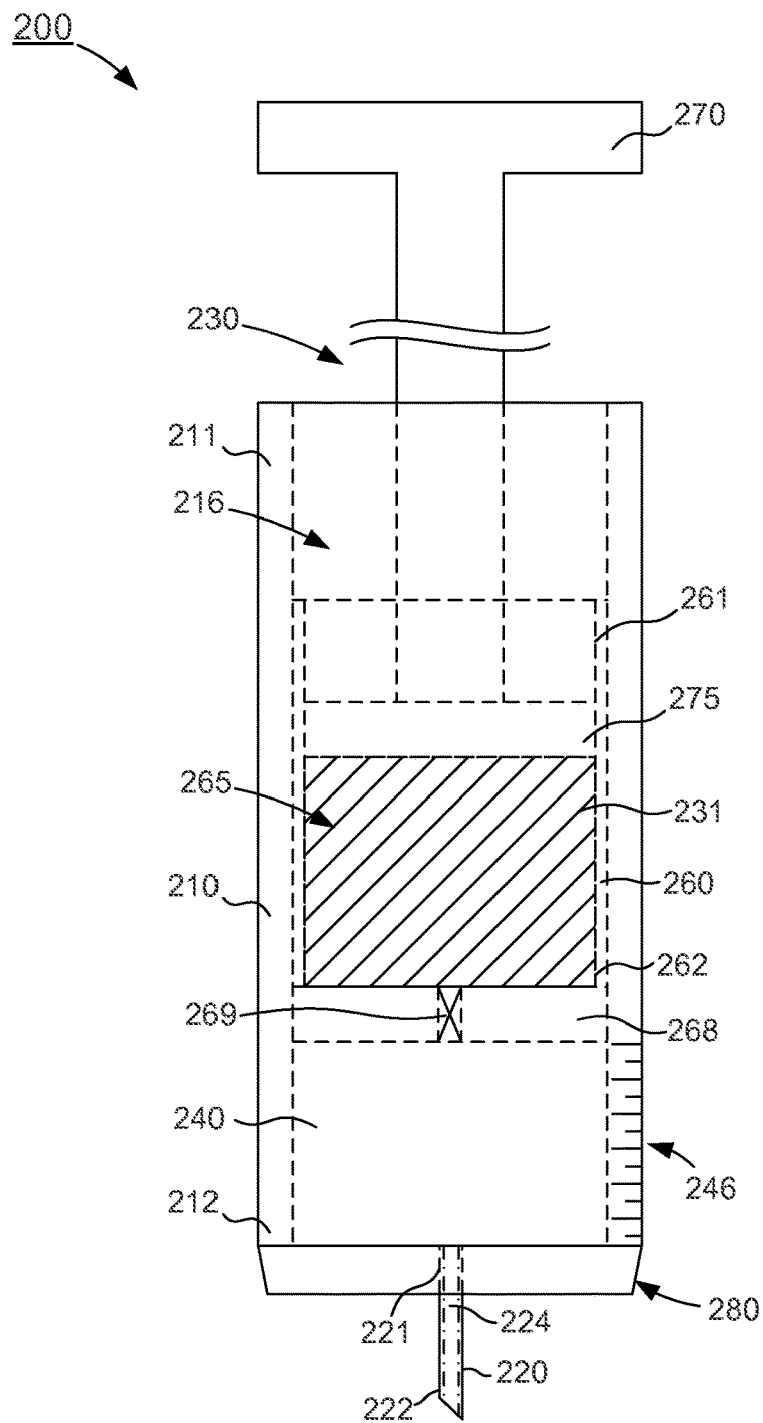
FIGS. 5-7 are schematic illustrations of a delivery device according to an embodiment in a first configuration, a second configuration, and a third configuration, respectively.
Figure 6:
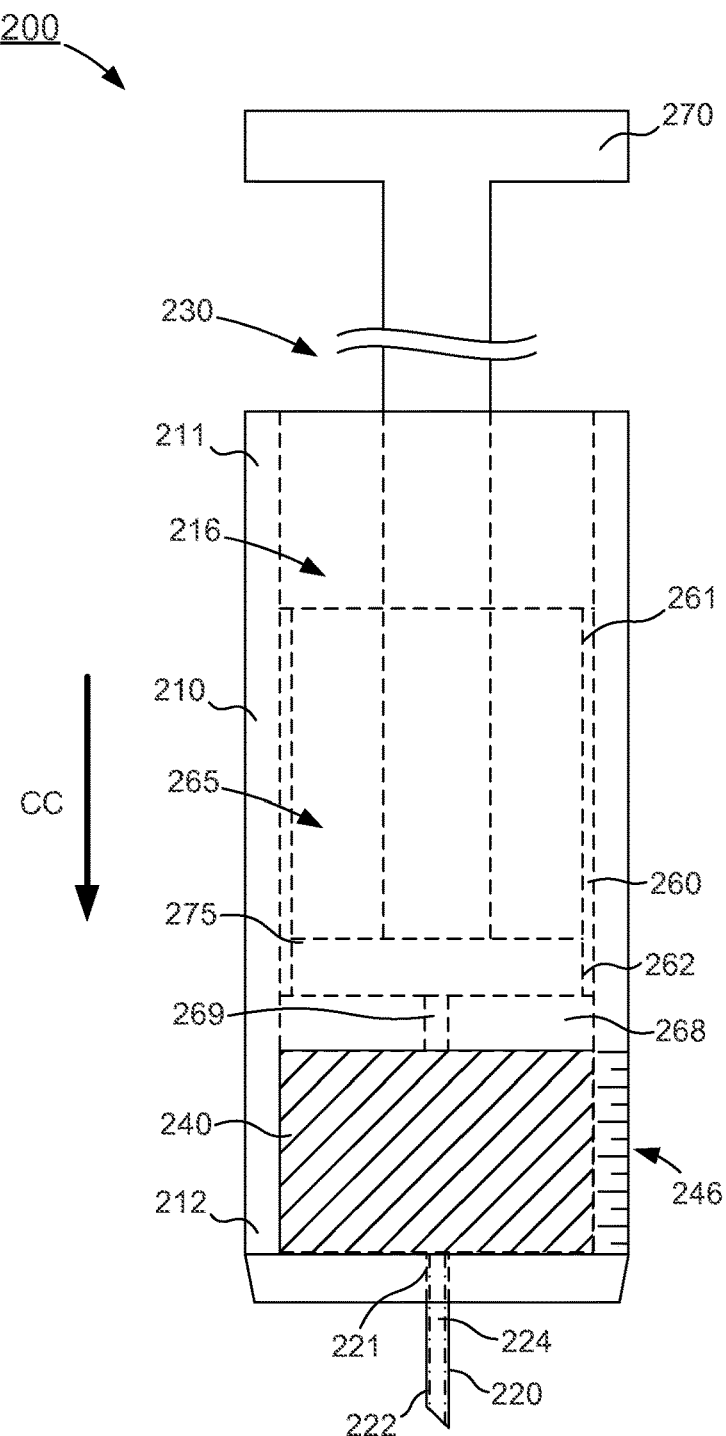
Figure 7:
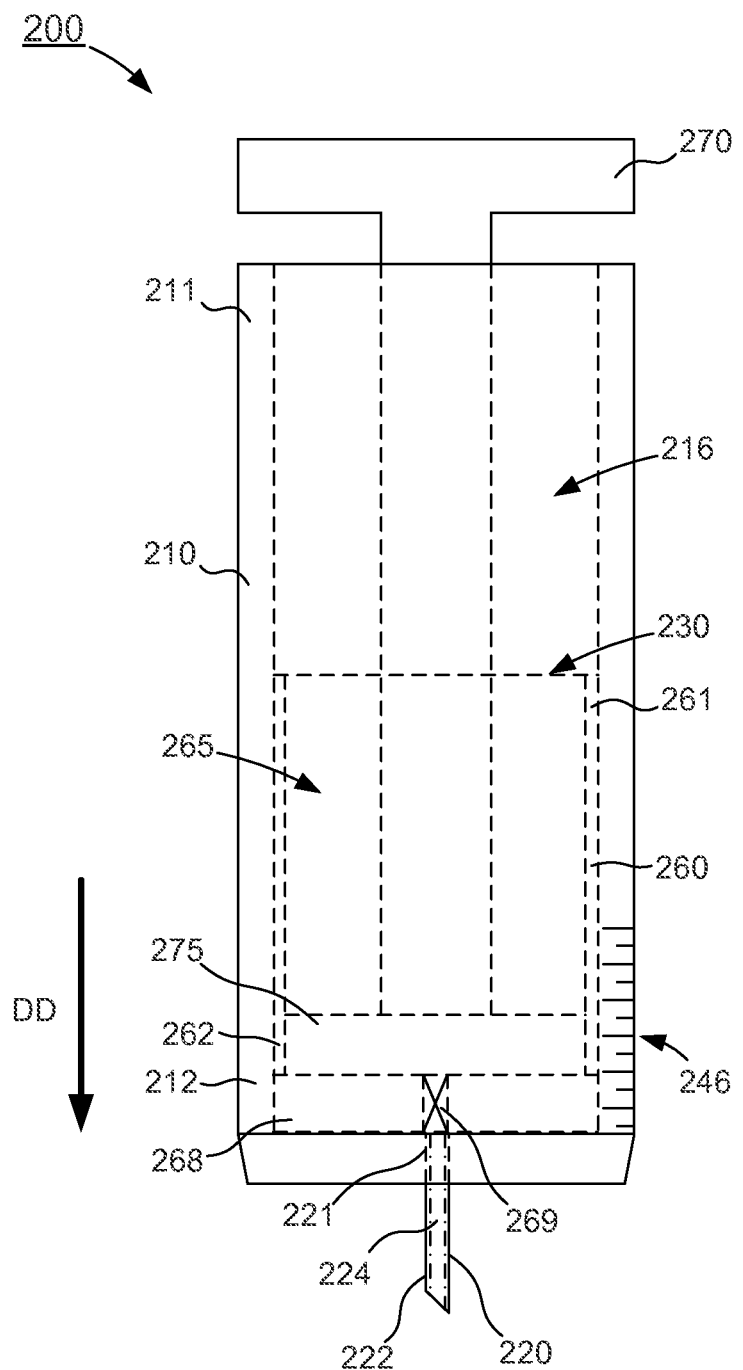

FIGS. 5-7 are schematic illustrations of a delivery device 200 according to an embodiment in a first configuration, a second configuration, and a third configuration, respectively. The delivery device 200 includes a housing 210, a puncture member 220, a cartridge assembly 230, and a huh assembly 280. The puncture member 220 defines a lumen 224 that extends through a proximal end portion 221 and a distal end portion 222. The distal end portion 222 of the puncture member 220 can include a bevel or a sharpened tip configured to puncture a target tissue of a patient. The proximal end portion 221 of the puncture member 220 is physically and fluidically coupled to the hub assembly 280, as described in further detail herein.

The puncture member 220 can be any suitable device that is configured to puncture, a target tissue of a patient. For example, the puncture member 220 can be a microneedle configured to puncture ocular tissue. In some embodiments, the puncture member 220 can be a 32-gauge microneedle or a 34-gauge microneedle. In some embodiments, such a microneedle can be substantially similar to or the same as the microneedles described in the '009 PCT application incorporated by reference above. In some embodiments, the shape and/or size of the puncture member 220 can correspond, at least partially, with at least a portion of a target tissue. For example, in some embodiments, the length of the puncture member 220 can correspond with a thickness of a portion of ocular tissue such that when the puncture member 220 is inserted into the ocular tissue, at least a portion of the puncture member 220 is disposed within the sclera or suprachoroidal space of the eye, as described in further detail herein.

The housing 210 has a proximal end portion 211 and a distal end portion 212 and defines an inner volume 216. The distal end portion 212 is physically and fluidically coupled to the hub assembly 280, as described in further detail herein. The proximal end portion 211 can be configured to receive the cartridge assembly 230. More specifically, at least a portion of the cartridge assembly 230 can be inserted through an opening defined by the proximal end portion 211 of the housing 210 to dispose at least a portion of the cartridge assembly 230 within the inner volume 216 of the housing 210.

The cartridge assembly 230 includes a first movable member 260 and a second movable member 270. As described in further detail herein, the cartridge assembly 230 can be moved between a first configuration (see e.g., FIG. 5), a second configuration (see e.g., FIG. 6), and a third configuration (see e.g., FIG. 7) to move the delivery device 200 between its first configuration, its second configuration, and its third configuration, respectively. The first movable member 260 has a proximal end portion 261 and a distal end portion 262 and defines an inner volume 265. The proximal end portion 261 of the first movable member 260 is substantially open to movably receive at least a portion of the second movable member 270. More specifically, at least a portion of the second movable member 270 is disposed within the inner volume 265 and can be moved between a first position (e.g., a proximal position (FIG. 5)) and a second position (e.g., a distal position (FIG. 6)). The second movable member 270 includes a seal member 275 (e.g., an elastomeric member or the like) that forms a friction fit with one or more surfaces of the first movable member 260 that define the inner volume 265. In this manner, the seal member 275 and the first movable member 260 can form a fluidic seal that substantially isolates a portion of the inner volume 265 that is distal to the seal member 275 from a portion of the inner volume 265 that is proximal to the seal member 275, as described in further detail herein.

The distal end portion 262 of the first movable member 260 is at least temporarily closed (e.g., at least temporarily fluidically sealed). In this manner, the inner volume 265 (e.g., the portion of the inner volume 265 between the seal member 275 and the distal end portion 262) of the first movable member 260 is fluidically isolated from a volume outside of the first movable member 260. Thus, the first movable member 260 and the second movable member 270 can collectively house and/or collectively form a first reservoir 231. The first reservoir 231 can contain a drug formulation of the compositions described herein (e.g., a prophylactic agent, a therapeutic agent, or a diagnostic agent). In some embodiments, the first reservoir 231 can contain a drug formulation with a volume of about 0.5 mL or less. In other embodiments, the first reservoir 231 can contain a drug formulation with a volume of about 0.1 mL. In still other embodiments, the first reservoir 231 can contain a drug formulation with a volume greater than about 0.5 mL.

The distal end portion 262 of the first movable member 260 further includes and/or forms a seal member 268. As described above with reference to the seal member 275, the seal member 268 can form a friction fit with one or more inner surfaces of the housing 210 that define the, inner volume 216. In this manner, the seal member 268 and the housing 210 can form a fluidic seal that substantially isolates a portion of the inner volume 216 that is distal to the seal member 268 from a portion of the inner volume 216 that is proximal to the seal member 268. Thus, the first movable member 260 and the housing 210 can collectively house and/or can collectively form a second fluid reservoir 240, as described in further detail herein.

In some embodiments, the distal end portion 262 of the first movable member 260 can be moved between a first configuration (e.g., a closed or sealed configuration) and a second configuration (e.g., an open configuration). For example, the distal end portion 262 of the first movable member 260 can include a valve 269 that can be moved between a first configuration (e.g., an closed configuration as shown in FIG. 5) and a second configuration (e.g., an open configuration as shown in FIG. 6). In some embodiments, the valve 269 can be a one way valve or the like. In other embodiments, the distal end portion 262 of the first movable member 260 can include a surface that can be deformed (e.g., punctured, broken, opened, or otherwise reconfigured) to expel the drug formulation contained within the first reservoir 231.

As described above, the distal end portion 212 of the housing 210 is physically and fluidically coupled to the hub assembly 280. For example, in some embodiments, the hub assembly 280 and the distal end portion 212 of the housing 210 can form a press fit, a snap fit, a threaded coupling, and/or the like. In other embodiments, the hub assembly 280 can be monolithically formed with the housing 210. As shown in FIG. 5, the hub assembly 280 is physically and fluidically coupled to the proximal end portion 221 of the puncture member 220. For example, in some embodiments, the proximal end portion 221 of the puncture member 220 can be disposed within a lumen (not shown in FIG. 5) defined by the hub assembly 280. In some embodiments, the hub assembly 280 can be over-molded about the proximal end portion 221 of the puncture member 220. In other embodiments, a delivery device can include a hub and a puncture member that are monolithically formed.

With the hub assembly 280 physically and fluidically coupled to the housing 210 and physically and fluidically coupled to the puncture member 220, the lumen 224 of the puncture member 220 is placed in fluid communication with the second reservoir 240. In some embodiments, the hub assembly 280 can include an adjustment mechanism or the like that can selectively control an effective shaft length of the puncture member 220. For example, in some embodiments, the hub assembly 280 can be arranged in a similar manner as those described in the U.S. patent application Ser. No. 14/268,687 entitled "Apparatus and Methods for Ocular Injection," and filed on May 2, 2014, the disclosure of which is incorporated herein by reference in its entirety.

In use, an operator (e.g., a doctor, technician, nurse, physician, ophthalmologist, etc.) can manipulate the delivery device 200 to insert the puncture member 220 into, for example, an ocular tissue. In some embodiments, the length of the puncture member 220 can at least partially correspond with the ocular tissue such that when inserted into the eye, the distal end portion 222 of the puncture member 220 is disposed within the suprachoroidal space. More specifically, the distal end portion 222 of the puncture member 220 pierces the sclera of the eye and is disposed within the sclera and/or the suprachoroidal space without substantially piercing the choroid of the eye.

With the puncture member 220 disposed within the eye, the cartridge assembly 230 can be moved from its first configuration to its second configuration to move the delivery device 200 from the first configuration (FIG. 5) to the second configuration (FIG. 6). For example, in some embodiments, the user can exert a force on the second movable member 270 that is sufficient to move the second movable member 270 from its first position (e.g., a proximal position) relative to the first movable member 260 toward its second position (e.g., a distal position) relative to the first movable member 260, as indicated by the arrow CC in FIG. 6.

In some embodiments, the force exerted by the user on the second movable member 270 can increase a pressure within the first reservoir 231 that is sufficient to move the valve 269 from its first configuration (e.g., the closed configuration, see FIG. 5) to its second configuration (e.g., the open configuration, see FIG. 6). For example, in some embodiments, the valve 269 can be configured to move from its first configuration to its second configuration when the pressure within the first reservoir 231 reaches or exceeds a given threshold. In other embodiments, the valve 269 can be manually moved between the first configuration and the second configuration via an actuator such as, for example, a toggle, a switch, a button, a slide, a rotational knob, etc. Therefore, when the valve 269 is placed in the second configuration, the first movable member 260 can define at least a portion of the flow path within which the drug can flow from the first reservoir 231 to the second reservoir 240. Expanding further, the seal member 268 disposed at the distal end portion 262 of the first movable member 260 fluidically isolates the first reservoir 231 from the second reservoir when the cartridge assembly 230 is in its first configuration. Thus, when the valve 269 is moved from its first configuration to its second configuration the substantially opened valve 269 defines the flow path that is otherwise obstructed while the cartridge assembly 230 is in its first configuration. The flow of the drug from the first reservoir 231 to the second reservoir 240 can be such that the drug is mixed and/or agitated when the drug flows from the first reservoir 231 to the second reservoir 240. Thus, the drug can be reconstituted such that the particles of the drug are no longer separated.

Although FIG. 6 shows that the entire amount of the drug within the first reservoir 231 flows into the second reservoir 240, in some instances, the flow of the drug from the first reservoir 231 to the second reservoir 240 can be metered such that a desired volume of the drug is disposed within the second reservoir 240. For example, in some embodiments, the housing 210 can include a volumetric indicator 246 or the like. More specifically, as shown in FIG. 6, the volumetric indicator 246 can be a set of markings (e.g., lines, tick marks, hash marks, dots, etc.) that can be associated with a fill volume of the second reservoir 240 and/or a dispense volume of the first reservoir 231. In this manner, the operator can monitor the volumetric indicator 246 as the drug flows into the second reservoir 240 and, in some instances, limit the volume of the drug that is transferred to the second reservoir 240. In other instances, substantially the entire volume of the drug within the first reservoir 231 can flow through the valve 269 to be disposed within the second reservoir 240. With the desired volume of the drug disposed in the second reservoir 240, the valve 269 can be moved from the second configuration (e.g., the open configuration) to the first configuration (e.g., the closed configuration). For example, in some instances, the pressure within the first reservoir 231 can fall below a given threshold that allows the valve 269 to move from the open configuration to the closed configuration. In other embodiments, the user can engage an actuator (not shown in FIGS. 5-7) to move the valve 269 from the second configuration to the first configuration. In some embodiments, the valve 269 can be moved from the second configuration to a third configuration. In such embodiments, the third configuration can be substantially similar to the first configuration (e.g., a closed configuration). In some embodiments, the valve 269 can be configured to remain substantially open once moved from the first configuration to the second configuration.

Once the desired volume of the drug is disposed within the second reservoir 240, the cartridge assembly 230 can be moved from its second configuration to its third configuration to move the delivery device 200 from the second configuration (FIG. 6) to the third configuration (FIG. 7). For example, in some embodiments, the user can exert a force on the second movable member 270 that is sufficient to move the first movable member 260 from a first position relative to the housing 210 (e.g., a proximal position) to a second position relative to the housing 210 (e.g., a distal position), as indicated by the arrow DD in FIG. 7. In some instances, a distal surface of the seal member 275 included in the second movable member 270 can be placed in contact with a proximal surface of the seal member 268 included in the first member 260 such that the first movable member 260 and the second movable member 270 move substantially concurrently to place the cartridge assembly 230 in the third configuration. In other instances, such as when only a portion of the volume of the drug is disposed within the second reservoir, the seal member 275 of the second movable member 270 can be spaced apart from the seal member 268 of the first movable member 260. In such instances, the valve 269 can be in the second configuration (e.g., closed) to fluidically isolate the first reservoir 231 from the second reservoir 240. Thus, the force that is exerted on the second movable member 270 can result in the distal surface of the seal member 275 exerting a pressure on a surface of the drug within the first reservoir 231 which can, in turn, transfer at least a portion of the force to the seal member 268 of the first movable member 260, thereby placing the cartridge assembly 230 in the third configuration (e.g., the drug is an incompressible fluid or a minimally compressible fluid).

With the lumen 224 of the puncture member 220 in fluid communication with the second reservoir 240, the movement of the cartridge assembly 230 from its second configuration to its third configuration expels the drug formulation (contained within the second reservoir 240, as described above) through the lumen 224 of the puncture member 220. Thus, the delivery device 200 can deliver a desired volume of a drug formulation to the suprachoroidal space of the eye and the drug formulation can flow within the suprachoroidal space to be delivered to, for example, the posterior region of the eye.

Figure 8:
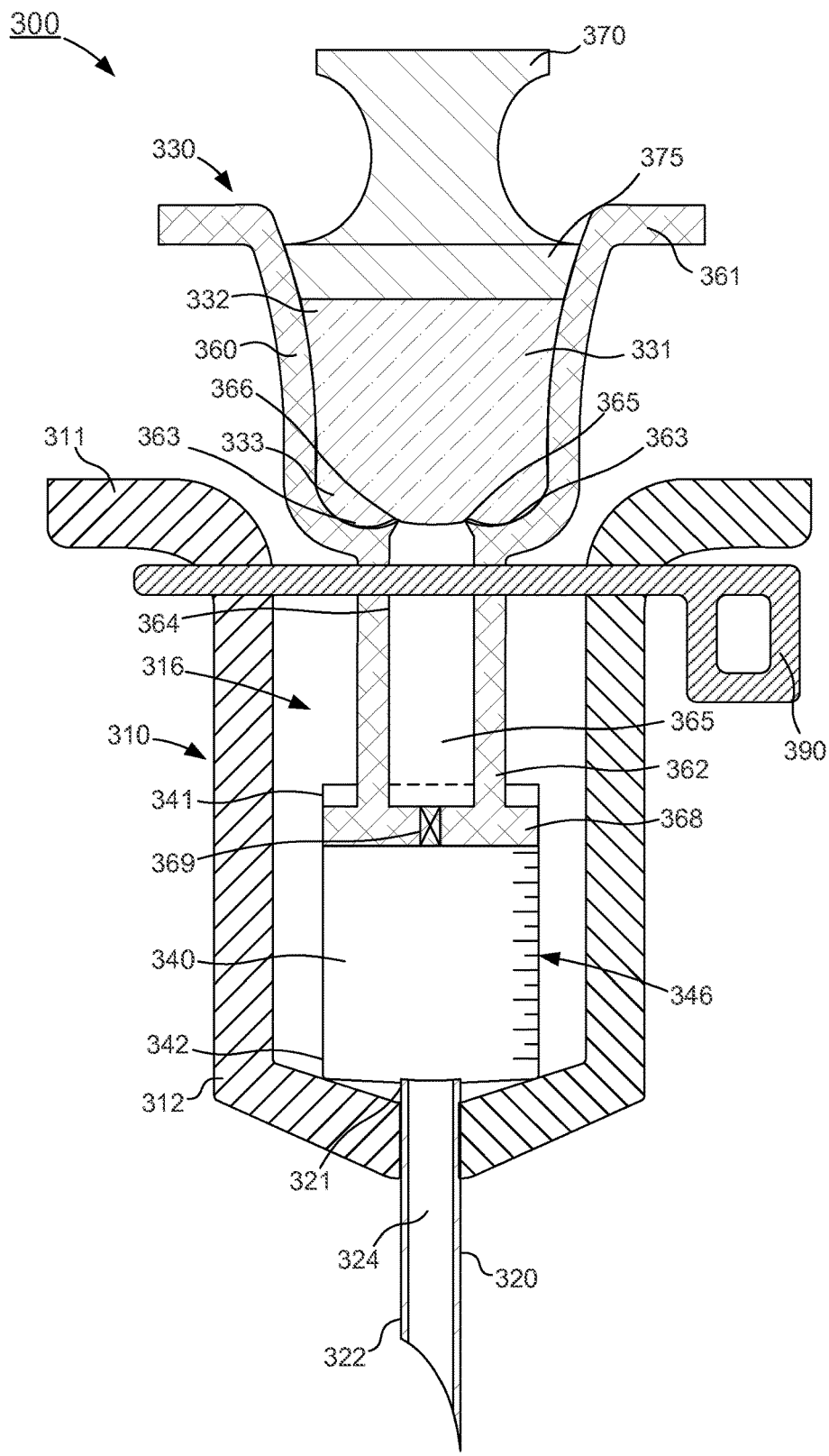
FIGS. 8-10 are schematic illustrations of a delivery device according to an embodiment in a first configuration, a second configuration, and a third configuration, respectively.
Figure 9:
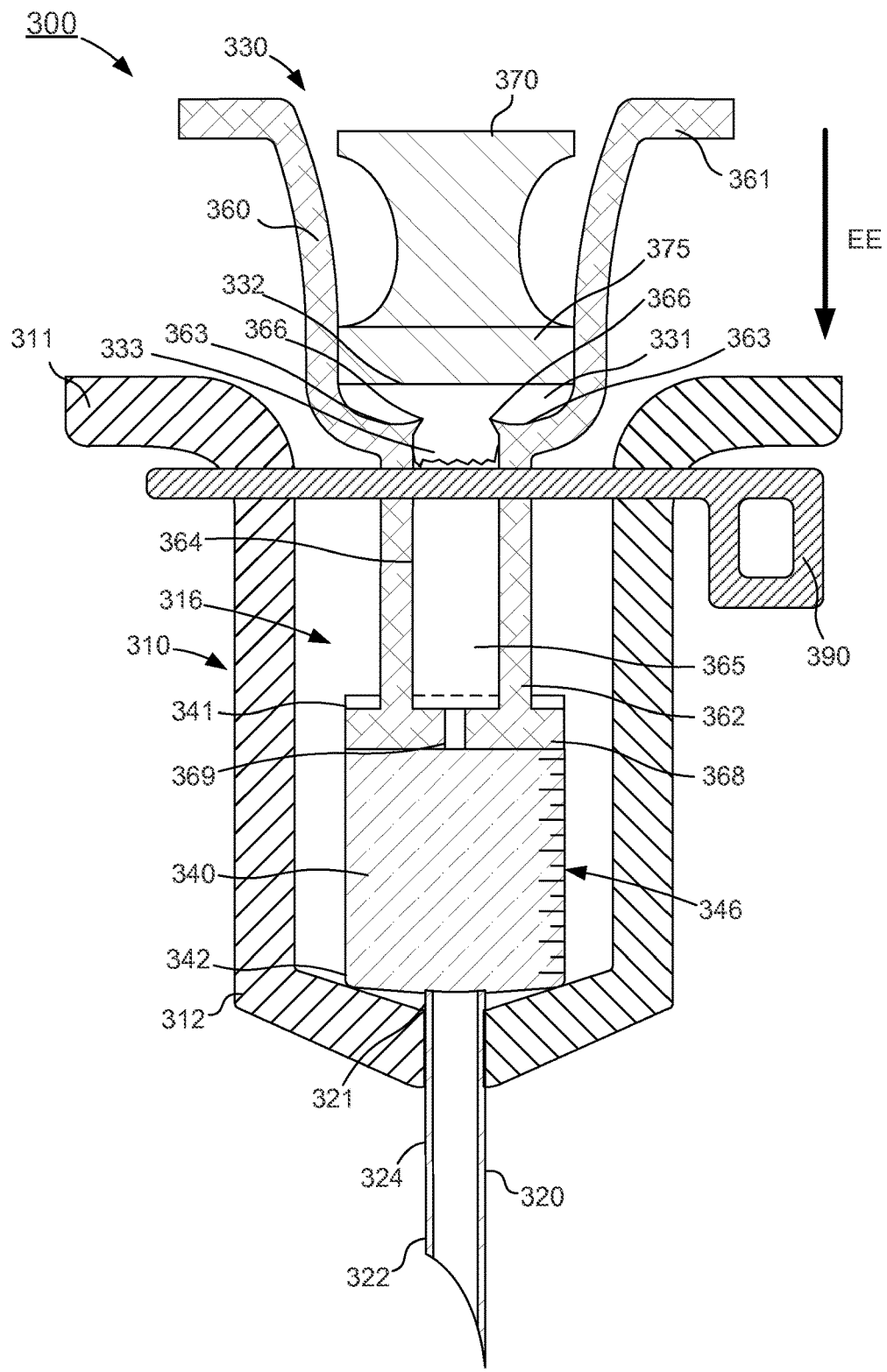
Figure 10:
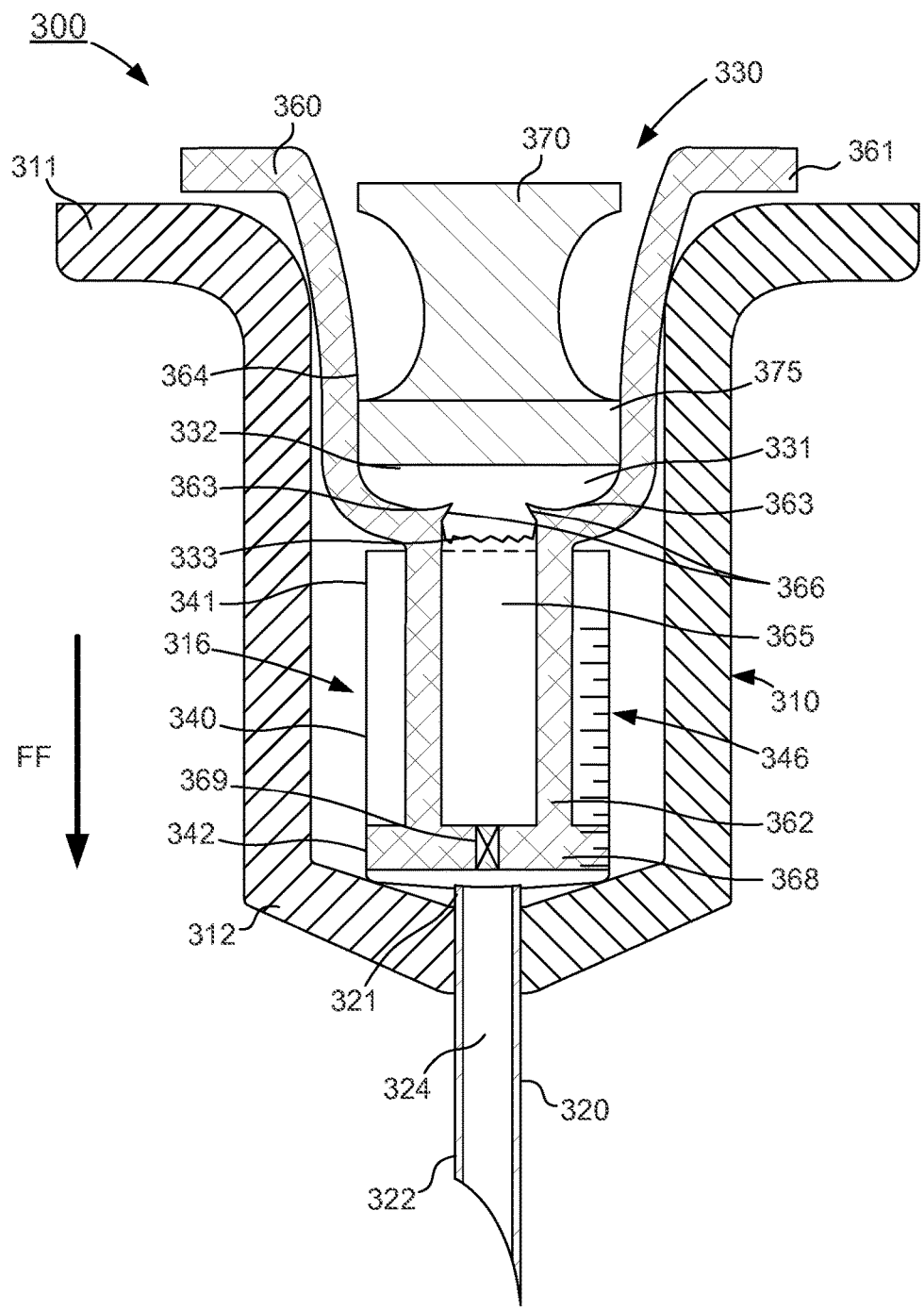

FIGS. 8-10 are schematic illustrations of a delivery device 300 according to another embodiment in a first configuration, a second configuration, and a third configuration, respectively. The delivery device 300 includes a housing 310, a puncture member 320, a cartridge assembly 330, a first reservoir 331, and a second reservoir 340. The housing 310 has a proximal end portion 311 and a distal end portion 312 and defines an inner volume 316. The proximal end portion 311 movably receives the cartridge assembly 330. More specifically, at least a portion of the cartridge assembly 330 is inserted through an opening defined by the proximal end portion 311 of the housing 310 to movably dispose at least a portion of the cartridge assembly 330 within the inner volume 316 of the housing 310. For example, in some embodiments, the delivery device 300 can be stored in a configuration in which the cartridge 330 (containing the drug) is spaced apart from and/or stored separately from the housing 310. In this manner, the cartridge 330 can be filled and/or stored in a different environment (e.g., filled in a clean room environment and stored in a refrigerated environment) from that in which the housing 310 is stored. The distal end portion 312 of the housing 310 is physically and fluidically coupled to the puncture member 320, as described in further detail herein.

As shown in FIG. 8, the housing 310 further includes a safety tab 390. For example, in some embodiments, at least a portion of the safety tab 390 can be disposed within a slot or the like (not shown) in the proximal end portion 311 of the housing 310 and can be arranged to selectively engage a portion of the cartridge assembly 330 to limit at least a distal movement of the cartridge assembly 330 relative to the housing 310. Expanding further, in some embodiments, the safety tab can be a substantially elongate member than can traverse the inner volume 316 of the housing 310 such that when the cartridge assembly 330 is inserted into the inner volume 316, the safety to 390 engages an outer surface of the cartridge assembly 330. Therefore, in use, an operator can manipulate the delivery device 300 to move the safety tab 390 relative to the housing 310 such that the portion of the safety tab 390 is removed from the inner volume 316, thereby allowing the cartridge assembly 330 to move relative to the housing 310, as described in further detail herein.

The puncture member 320 can be configured to puncture and/or penetrate a portion of the eye to deliver a drug formulation to, for example, the suprachoroidal space. In some embodiments, the puncture member 320 can be a 32-gauge microneedle or a 34-gauge microneedle. The puncture member 320 has a proximal end portion 321 and a distal end portion 322, and defines a lumen 324. As shown in FIG. 8, the proximal end portion 321 is coupled to the distal end portion 312 of the housing 310 and can be arranged such that the lumen 324 is placed in fluid communication with the second reservoir 340. More specifically, the puncture member 320 extends from the distal end portion 312 of the housing 310 in the distal direction to define an effective shaft length that can substantially correspond to at least a portion of the eye, as described above. In some embodiments, the distal end portion 322 can be substantially similar to or the same as those described in the '009 PCT application incorporated by reference above. In this manner, the distal end portion 322 of the puncture member 320 can pierce ocular tissue while minimizing deformation of the tissue at or near the insertion site. In some embodiments, the puncture member 320 can be substantially similar to the puncture member 220 described above with reference to FIGS. 5-7. Thus, the puncture member 320 is not described in further detail herein.

The cartridge assembly 330 includes a first movable member 360 and a second movable member 370. As described in further detail herein, the cartridge assembly 330 can be moved between a first configuration (FIG. 8), a second configuration (FIG. 9), and a third configuration (FIG. 10) to move the delivery device 300 between its first configuration, its second configuration, and its third configuration, respectively. The first movable member 360 has a proximal end portion 361 and a distal end portion 362 and defines an inner volume 365. The first movable member 360 can be any suitable shape, size, or configuration. For example, in some embodiments, the first movable member 360 can have a substantially cylindrical shape. The proximal end portion 362 of the first movable member 360 is substantially open to movably receive the first reservoir 331 and at least a portion of the second movable member 370. For example, at least a portion of the second movable member 370 is disposed within the inner volume 365 and can be moved between a first position (e.g., a proximal position, see FIG. 8) and a second position (e.g., a distal position, see FIG. 9), as described in further detail herein. Similarly, the first reservoir 331 can be moved, within the inner volume 365, between a first configuration (see e.g., FIG. 8) and a second configuration (see e.g., FIG. 9), as described in further detail herein.

The first movable member 360 includes an inner surface 364 that defines the inner volume 365. In some embodiments, at least a portion of the second movable member 370 can be in contact with the inner surface 364. For example, in some embodiments, the second movable member 370 includes a seal member 375 that forms a friction fit with the inner surface 364 of the first movable member 360. In this manner, the seal member 375 and the first movable member 360 can form a substantially fluidic seal that can fluidically isolate a portion of the inner volume 365 that is distal to the seal member 375 from a portion of the inner volume 365 that is proximal to the seal member 375, as described in further detail herein.

In some embodiments, the inner surface 364 of the first movable member 360 is substantially cylindrical and includes and/or firms one or more shoulders 363. In some embodiments, the shoulder 363 can be formed by a change in a diameter of the inner surface 364. For example, a first portion of the inner surface 364 (e.g., a distal end portion) can have a first diameter and a second portion of the inner surface 364 (e.g., a proximal end portion) can have a second diameter that is greater than the first diameter. Therefore, the change in the diameter of the inner surface 364 forms a substantially annular shoulder 363. In some embodiments, the shoulder 363 is continuous (e.g., the shoulder 363 circumscribes the inner surface 364). In other embodiments, a first movable member can have an inner surface that can form one or more shoulders that are discontinuous.

As shown in FIG. 8, the shoulder 363 is in contact with an outer surface of the first reservoir 331, when the first reservoir 331 is disposed within the inner volume 365. Moreover, the shoulder 363 can form and/or can include one or more protrusions 366 that can be operative in moving the first reservoir 331 from the first configuration to the second configuration. For example, in some embodiments, the protrusions 366 formed by the shoulder 363 can be a barbed surface that can pierce or puncture a portion of the outer surface of the first reservoir 331 to move the first reservoir 331 from the first configuration to the second configuration, as described in further detail herein. In some embodiments, an outer surface of the shoulder 363 can be in contact with the safety tab 390 (described above) to selectively limit movement of the first movable member 360, as described in further detail herein.

The distal end portion 362 of the first movable member 360 is at least temporarily closed (e.g., at least temporarily fluidically sealed). In this manner, the inner volume 365 (e.g., the portion of the inner volume 365 between the seal member 375 and the distal end portion 362) of the first movable member 360 is selectively fluidically isolated from a volume outside of the first movable member 360. For example, the distal end portion 362 includes a valve 369 that can be moved between a first configuration (e.g., a closed or sealed configuration (see e.g., FIG. 8)) and a second configuration (e.g., an open configuration (see e.g., FIG. 9)). In some embodiments, the valve 369 can be a one way valve or the like (e.g., a check valve such as, for example, a ball valve, a diaphragm valve, a stop valve, a duckbill valve, or the like). In this manner, the sterility of the inner volume 365 between the seal member 375 and the distal end portion 362 of the first movable member 360 can be maintained prior to the valve 369 being moved to the second configuration.

As shown in FIGS. 8-10, the distal end portion 362 is movably disposed within a portion of the second reservoir 340. For example, the distal end portion 362 of the first movable member 360 can be moved from a first position within the second reservoir 340 (e.g., a proximal position, see FIG. 9) to a second position within the second reservoir (e.g., a distal direction, see FIG. 10), when the second movable member 370 is moved from its first position to its second position relative to the housing 310. As described above with reference) to the seal member 375, the distal end portion 362 of the first movable member 360 includes a seal member 368 that forms a friction fit with an inner surface of the second reservoir 340. In this manner, the seal member 368 and the inner surface of the second reservoir 340 form a substantially fluid tight seal that isolates a portion of the second reservoir 340 that is distal to the seal member 368 from a portion of the second reservoir 340 that is proximal to the seal member 368.

The first reservoir 331 of the delivery device 300 has a proximal end portion 332 and a distal end portion 333 and is movable between its first configuration (FIG. 8) and its second configuration (FIGS. 9 and 10), as described above. The first reservoir 331 can be any suitable shape, size, or configuration. For example, in some embodiments, the first reservoir 331 can be a pouch, a fillable bag, a deformable package, a deformable vial, or the like. The first reservoir 331 is arranged within the inner volume 365 of the first movable member 360 such that the proximal end portion 332 of the fluid reservoir 331 is at least temporarily in contact with the seal member 375 of the second movable member 370 and the distal end portion 333 of the first reservoir 331 is at least temporarily in contact with the shoulder 363 of the first movable member 360. In this manner, the first reservoir 331 can be moved from its first configuration to its second configuration by deforming at least a portion of the first reservoir 331. More specifically, the first reservoir 331 contains a drug formulation of the compositions described herein (e.g., a prophylactic agent, a therapeutic agent, or a diagnostic agent) when in the first configuration, and can be moved to the second configuration to allow the drug formulation to be expelled from within the first reservoir 331. In some embodiments, when in the first configuration, the first reservoir 331 can contain a drug formulation with a volume of about 0.5 mL or less. In other embodiments, the first reservoir 331 can contain a drug formulation with a volume of about 0.1 mL. In still other embodiments, the first reservoir 331 can contain a drug formulation with a volume greater than about 0.5 mL.

The second reservoir 340 of the delivery device 300 has a proximal end portion 341 and a distal end portion 342. The second reservoir 340 can be any suitable shape, size, or configuration. For example, in some embodiments, the second reservoir 340 can be a vial that is a substantially rigid container that can define any suitable sized volume configured to receive the drug formulation. Moreover, the second reservoir 340 can include a volumetric indicator 346 that can provide a user with an indication of an amount of drug formulation disposed therein, as described above with reference to the volumetric indicator 246 of FIGS. 5-7.

The second reservoir 340 is disposed within the inner volume 316 of the housing 310 and can be placed in fluid communication with the lumen 324 of the puncture member 340. For example, in some embodiments, the proximal end portion 321 of the puncture member 320 can be physically and fluidically coupled to the second reservoir 340 such that the lumen 324 of the puncture member 320 is maintained in constant fluid communication with the second reservoir 340. In other embodiments, the lumen 324 of the puncture member 320 can have a sufficiently small diameter such that a drug formulation will not substantially flow through the lumen 324 of the puncture member 320 unless the pressure within the second reservoir 340 is increased beyond a given threshold. In other embodiments, the second reservoir 340 and/or the puncture member 320 can include a valve, a breakable seal, or the like that can be moved from a first configuration (e.g., a closed configuration), where the second reservoir 340 is fluidically isolated from the puncture member 320, to a second configuration (e.g., an open configuration), where the second reservoir 340 is in fluid communication with the lumen 324 of the puncture member 320. Therefore, a drug formulation can be urged to flow from the second reservoir 340 through the lumen 324 of the puncture member 320 to be delivered to a target tissue (e.g., the suprachoroidal space of the eye), as described in further detail herein.

In use, an operator (e.g., a doctor, technician, nurse, physician, ophthalmologist, etc.) can manipulate the delivery device 300 to insert the puncture member 320 into, for example, an ocular tissue. In some embodiments, the length of the puncture member 320 can at least partially correspond with ocular tissue such that, when inserted into the eye, the distal end portion 322 of the puncture member 320 is disposed within the suprachoroidal space. More specifically, the distal end portion 322 of the puncture member 320 pierces the sclera of the eye and is disposed within the sclera and/or the suprachoroidal space without substantially piercing the choroid of the eye (see e.g., FIG. 1 for anatomical context). With the puncture member 320 disposed within the eye, the cartridge assembly 330 can be moved from its first configuration to its second configuration to move the delivery device 300 from the first configuration (FIG. 8) to the second configuration (FIG. 9). For example, in some embodiments, the user can exert a force on the second movable member 370 that is sufficient to move the second movable member 370 from its first position (e.g., a proximal position) relative to the first movable member 360 toward its second position (e.g., a distal position) relative to the first movable member 360, as indicated by the arrow EE in FIG. 9. Expanding further, in some embodiments, the proximal end portion 361 of the first movable member 360 can include an engagement portion (e.g., a flange) that can be engaged by the user to limit movement of the first movable member 360. Moreover, with the first movable member 360 in contact with the safety tab 390, the safety tab 390 can also limit movement of the first movable member 360. Therefore, the second movable member 370 can be moved relative to the first movable member 360 without substantially moving the first movable member 360 relative to the housing 310. In some embodiments, the cartridge assembly 330 can be moved from its first configuration to its second configuration before the puncture member 320 is disposed within the eye.

With the first reservoir 331 bounded by (e.g., in contact with) the seal member 375 of the second movable member 370, and the inner surface 364 of the first movable member 360, the force exerted by the user on the second movable member 370 compresses the first reservoir 331 between the second movable member 370 and the shoulder 363. In this manner, the protrusions 366 that extend from the shoulders 363 puncture the distal end portion 333 of the first reservoir 331 to move the first reservoir 331 from its first configuration to its second configuration, as shown in FIG. 9. Thus, the fluid reservoir 331 is placed in fluid communication with the inner volume 365 of the first movable member 360.

With the first reservoir 331 in the second configuration, the valve 369 can be moved from its first configuration (e.g., the closed configuration, see FIG. 8) to its second configuration (e.g., the open configuration, see FIG. 9). For example, in some embodiments, the valve 369 can move from the first configuration to the second configuration when the pressure within the portion of the inner volume 365 between the seal member 375 and the distal end portion 362 of the first movable member 360 reaches or exceeds a given threshold. In other embodiments, the valve 369 can be manually moved between the first configuration and the second configuration via an actuator such as, for example, a toggle, a switch, a button, a slide, a rotational knob, etc (not shown in FIGS. 8-10). Therefore, when the valve 369 is placed in the second configuration, the first movable member 360 can define at least a portion of the flow path within which the drug can flow from the first reservoir 331 to the second reservoir 340 that would otherwise be obstructed while the cartridge assembly 330 is in its first configuration. The flow of the drug from the first reservoir 331 to the second reservoir 340 can be such that the drug is mixed and/or agitated when the drug flows from the first reservoir 331 to the second reservoir 340. Thus the drug can be reconstituted such that the particles of the drug are no longer separated.

Although FIG. 9 shows that the entire amount of the drug within the first reservoir 331 flows into the second reservoir 340, in some instances, the flow of the drug from the first reservoir 331 to the second reservoir 340 can be metered such that a desired volume of the drug is disposed within the second reservoir 340. For example, in some embodiments, the second reservoir 340 can include a volumetric indicator 346 or the like. In this manner, the operator can monitor the volumetric indicator 346 as the drug flows into the second reservoir 340 and, in some instances, limit the volume of the drug that is transferred to the second reservoir 340. With the desired volume of the drug disposed in the second reservoir 340 the valve 369 can be moved from the second, open configuration to the first, closed configuration (as described in detail above with reference to the valve 268 shown in FIG. 6).

Once the desired volume of the drug is disposed within the second reservoir 340 and the valve 369 is in its first configuration, the safety tab 390 can be removed from the housing 310 or otherwise disengaged from the first movable member 360 to allow the cartridge assembly 330 to be moved from its second configuration (FIG. 9) to its third configuration (FIG. 10) to move the delivery device 300 from the second configuration to the third configuration. For example, in some embodiments, the user can remove the safety tab 390 and can exert a force on the first movable member 360 that is sufficient to move the first movable member 360 from a first position relative to the housing 310 (e.g., a proximal position) to a second position relative to the housing 310 (e.g., a distal position), as indicated by the arrow FF in FIG. 10. Expanding further, in some embodiments, the proximal end portion 311 of the housing 310 can include an engagement portion (e.g., a flange) that can be engaged to limit movement of the housing 310. Therefore, the first movable member 360 can be moved relative to the housing 310 without substantially moving the housing 310.

With the second reservoir 340 coupled to the housing 310, the distal movement (e.g., in the FF direction) of the first movable member 360 is such that the distal end portion 362 of the first movable member 360 moves within the second reservoir 340. Furthermore, with the seal member 368 forming a substantially fluid tight seal with the inner surface of the second reservoir 340, the distal movement of the seal member 368 exerts a pressure on a surface of the drug within the second reservoir 340 that is sufficient to expel the drug formulation through the lumen 324 of the puncture member 320. For example, in some embodiments, the pressure exerted on the surface of the drug formulation can increase the pressure within the second reservoir 340 to a pressure that is sufficient to open a valve (not shown) of the second reservoir 340 and/or of the puncture member 320 (as described above). Thus, the delivery device 300 can deliver a desired volume of a drug formulation to the suprachoroidal space of the eye and the drug formulation can flow within the suprachoroidal space to be delivered to, for example, the posterior region of the eye.

Figure 11:
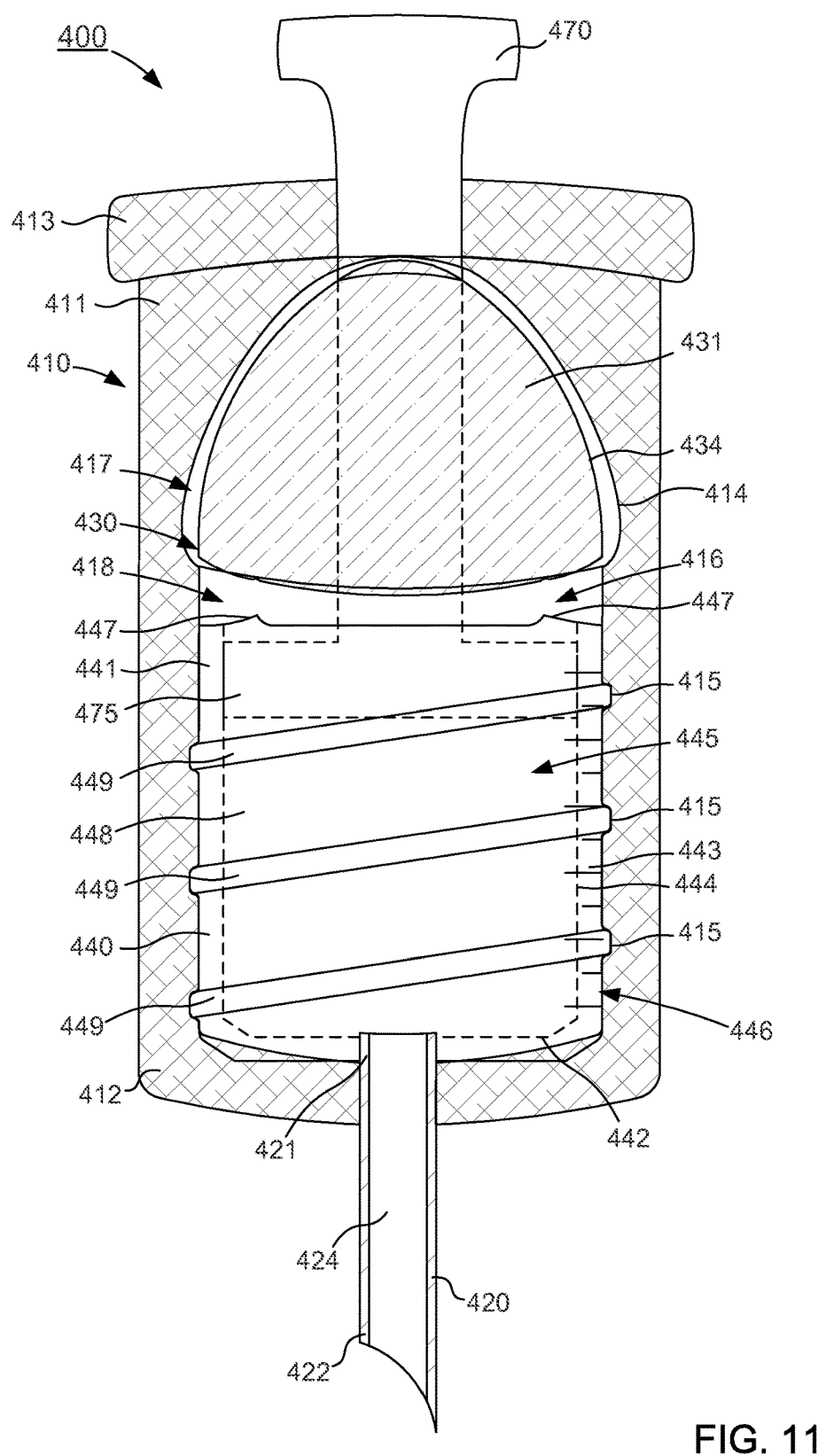
FIGS. 11-13 are schematic illustrations of a delivery device according to an embodiment in a first configuration, a second configuration, and a third configuration, respectively.
Figure 12:
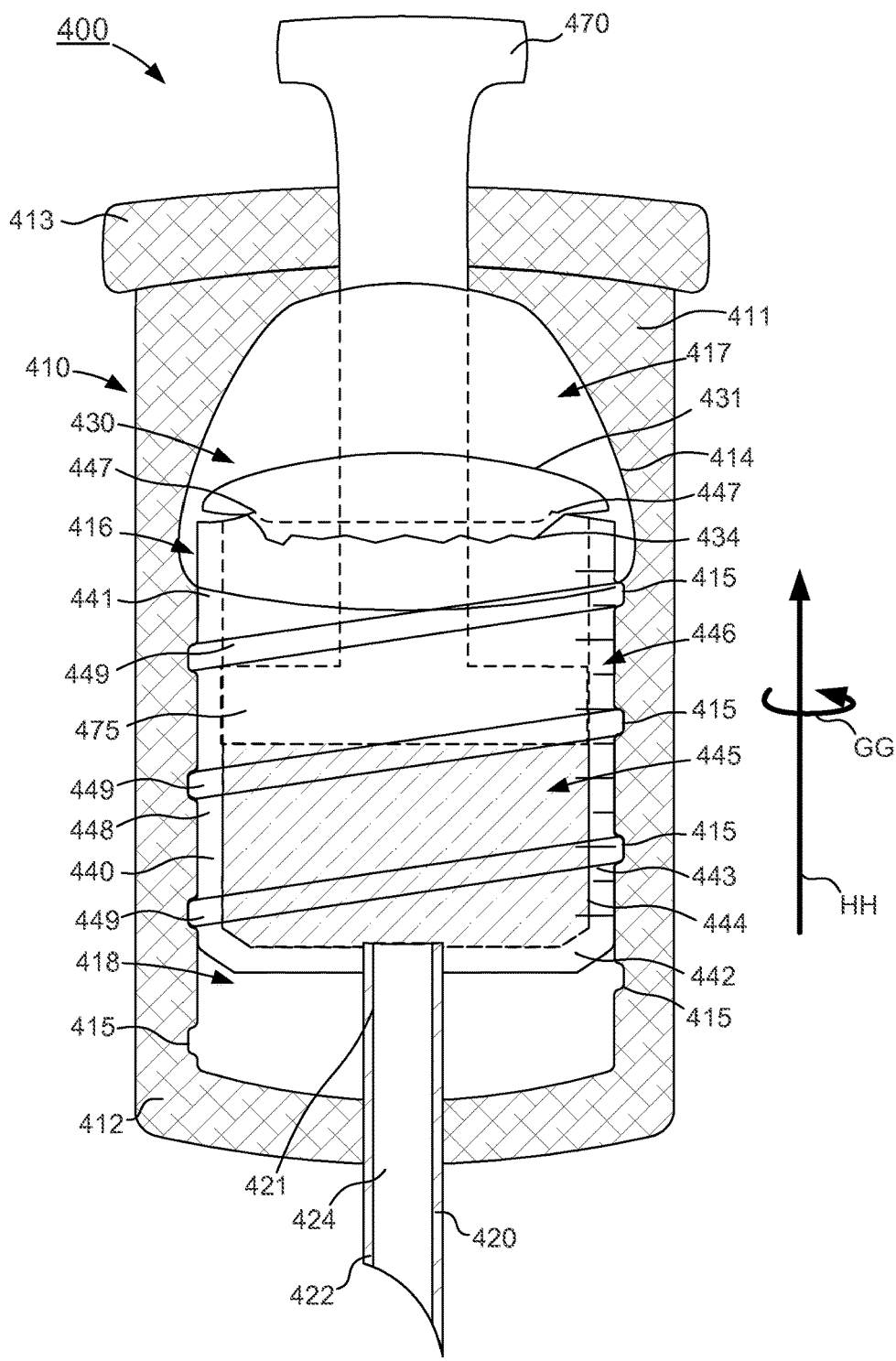
Figure 13:
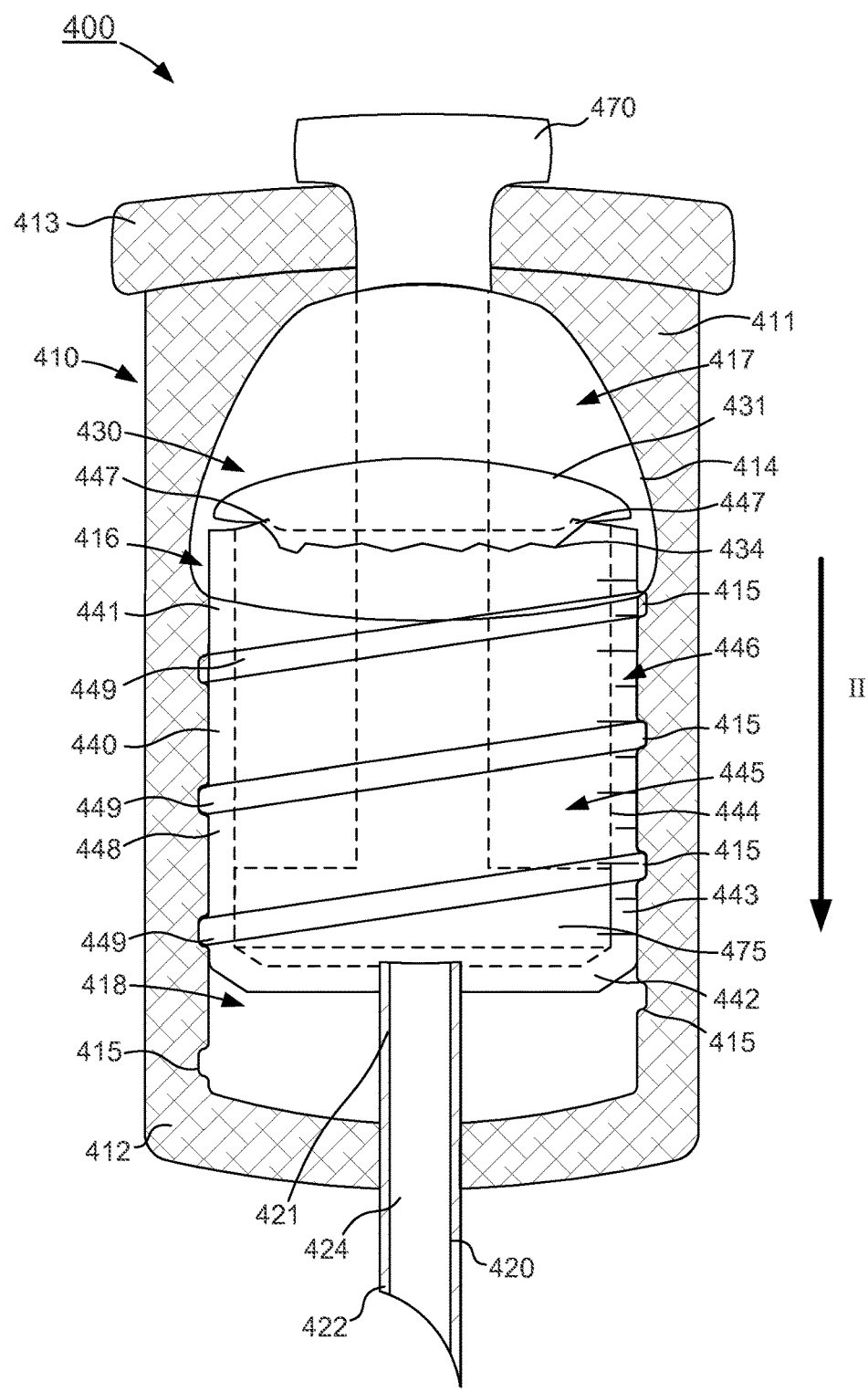

FIGS. 11-13 are schematic illustrations of a delivery device 400 according to another embodiment in a first configuration, a second configuration, and a third configuration, respectively. The delivery device 400 includes a housing 410, a puncture member 420, and a cartridge assembly 430. The housing 410 has a proximal end portion 411 and a distal end portion 412 and defines an inner volume 416. More particularly, the housing 410 includes an inner surface 414 that defines the inner volume 416. The inner volume 416 is configured to receive and/or house at least a portion of the cartridge assembly 430. The distal end portion 412 can movably receive a portion of the puncture member 420. For example, although not shown in FIGS. 11-13, in some embodiments, the distal end portion 412 of the housing 410 can include an opening, a channel, a slot, etc. that can movably receive the portion of the puncture member 420. The proximal end portion 411 can include and/or can be coupled to an engagement portion 413, as described in further detail herein.

The puncture member 420 can be configured to puncture and/or penetrate a portion of the eye to deliver a drug formulation to, for example, the suprachoroidal space. The puncture member 420 has a proximal end portion 421 and a distal end portion 422, and defines a lumen 424. As shown in FIG. 11, the proximal end portion 421 is physically and fluidically coupled to a portion of the cartridge assembly 430, as described in further detail herein. In some embodiments, the distal end portion 422 can be substantially similar to or the same as those described in the '009 PCT application incorporated by reference above. In this manner, the distal end portion 412 of the puncture member 410 can pierce ocular tissue while minimizing deformation of the tissue at or near the insertion site In some embodiments, the puncture member 420 can be substantially similar to the puncture member 220 described above with reference to FIGS. 5-7. Thus, the puncture member 420 is not described in further detail herein.

The cartridge assembly 430 includes a first reservoir 431, a second reservoir 440, and a plunger 470. The cartridge assembly 430 is disposed within the inner volume 416 of the housing 410 and can be moved between a first configuration (FIG. 11), a second configuration (FIG. 12), and a third configuration (FIG. 13) to move the delivery device 400 between its first configuration, its second configuration, and its third configuration, respectively. More specifically, a first portion 417 of the inner volume 416 is configured to house the first reservoir 431 of the cartridge assembly 430. Similarly, a second portion 418 of the inner volume 416 is configured to house the second reservoir 440 included in the cartridge assembly 430.

The first reservoir 431 of the cartridge assembly 430 has a proximal end portion 432 and a distal end portion 433 and can be movable between a first configuration (FIG. 11) and a second configuration (FIGS. 12 and 13), as described above. The first reservoir 431 can be any suitable shape, size, or configuration. In some embodiments, the first reservoir 431 can have a shape that substantially corresponds with a shape of the inner surface 414 of the housing 410 that defines the first portion 417 of the inner volume 416. For example, in some embodiments, the first reservoir 430 can be a pouch or the like and can have a shape, when filled with a drug formulation, that substantially corresponds with the shape of the first portion 417 of the inner volume 416 (e.g., substantially conical). When in the first configuration, the first reservoir 431 can contain any suitable drug formulation such as any of the compositions described herein, and when moved to the second configuration, the first reservoir 431 can allow the drug formulation to be expelled from within the first reservoir 431. In some embodiments, when in the first configuration, the first reservoir 431 can contain a drug formulation with a volume of about 0.5 mL, or less. In other embodiments, the first reservoir 431 can contain a drug formulation with a volume of about 0.1 mL. In still other embodiments, the first reservoir 431 can contain a drug formulation with a volume greater than about 0.5 mL.

The second reservoir 440 has a proximal end portion 441 and a distal end portion 442 and defines an inner volume 445. More specifically, the second reservoir 440 has a set of walls 443 that have an outer surface 448 and an inner surface 444, which defines the inner volume 445. The second reservoir 440 (analogous to a first movable member) of the cartridge assembly 430 is disposed within the second portion 418 of the inner volume 416 and is movable between a first position (FIG. 11) and a second position (FIG. 12), relative to the housing 410. For example, as shown in FIG. 11, the outer surface 448 of the second reservoir 440 includes a set of threads 449 that can engage a set of threads 415 defined by the inner surface 414 of the housing 410. In this manner, the second reservoir 440 can be rotated relative to the housing 410 to advance the threads 449 of the second reservoir 440 along the threads 415 of the housing 410, thereby moving the second reservoir 440 between its first position and its second position, relative to the housing 410. Moreover, the outer surface 448 of the second reservoir 440 includes a set of protrusions 447 (e.g., barbs or the like as described above with reference to the first movable member 360 of FIGS. 8-10) along a proximal edge that are placed in contact with the distal end portion 432 of the first reservoir 431. In this manner, the protrusions 447 are operable in moving the first reservoir 431 from its first configuration to its second configuration, as described in further detail herein.

The distal end portion 442 of the second reservoir 440 is substantially closed and is coupled to the proximal end portion 421 of the puncture member 420. In this manner, the lumen 424 defined by the puncture member 420 can be selectively placed in fluid communication with the inner volume 445 of the second reservoir 440, as described in further detail herein. The proximal end portion 442 of the second reservoir 440 is substantially open to movably receive at least a portion of the plunger 470. For example, at least a portion of the plunger 470 (analogous to a second movable member) is disposed within the inner volume 445 and can be moved between a first position (e.g., a proximal position) and a second position (e.g., a distal position). More specifically, the plunger 470 includes a seal member 475 that forms a friction fit with the inner surface 444 of the walls 443. In this manner, the seal member 475 and the second reservoir 440 can form a substantially fluid tight seal that can fluidically isolate a portion of the inner volume 445 that is distal to the seal member 475 from a portion of the inner volume 445 that is proximal to the seal member 475.

In use, an operator (e.g., a doctor, technician, nurse, physician, ophthalmologist, etc.) can manipulate the delivery device 400 to insert the puncture member 420 into, for example, ocular tissue. In some embodiments, the length of the puncture member 420 can at least partially correspond with the ocular tissue such that, when inserted into the eye, the distal end portion 422 of the puncture member 420 is disposed within the suprachoroidal space. More specifically, the distal end portion 422 of the puncture member 420 pierces the sclera of the eye and is disposed within the sclera and/or the suprachoroidal space without substantially piercing the choroid of the eye (see e.g., FIG. 1 for anatomical context). With the puncture member 420 disposed within the eye, the cartridge assembly 430 can be moved from its first configuration (FIG. 11) to its second configuration (FIG. 12) to move the delivery device 400 from the first configuration to the second configuration. For example, in some embodiments, the user can manipulate the engagement portion 413 of the housing 410 to rotate the housing 410 relative to the second reservoir 440 (or vice versa), as indicated by the arrow GG in FIG. 12. In this manner, the threads 440 of the second reservoir 440 are advanced along the threads 415 of the housing 410 to move the second reservoir 440 from its first position (e.g., a distal position) relative to the housing 410 toward its second position (e.g., a proximal position) relative to the housing 410. as indicated by the arrow HH.

The proximal movement of the second reservoir 440 relative to the housing 410 can be such that the second reservoir 440 is placed in contact with the first reservoir 431 disposed within the first portion 417 of the inner volume 416, In this manner, the protrusions 447 that extend from the proximal surface of the second reservoir 440 puncture the distal end portion 433 of the first reservoir 431, thereby moving the first reservoir 431 from its first configuration to its second configuration, as shown in FIG. 12. Thus, the fluid reservoir 431 is placed in fluid communication with the inner volume 445 of the second reservoir 440. For example, although not shown in FIGS. 11-13, the seal member 475 of the plunger 470 and/or the inner surface 444 of the second reservoir 440 can include and/or can define a fluid flow path that can selectively place the first reservoir 431 (when the first reservoir 431 is in its second configuration) in fluid communication with a portion of the inner volume 445 of the second reservoir 440 that is distal to the seal member 475. By way of example, in some embodiments, the seal member 475 can include a valve (not shown in FIGS. 11-13) that can be moved from a closed configuration to an open configuration, as described above with reference to the valve 369 of the first movable member 360 shown in FIG. 9. The flow of the drug from the first reservoir 431 to the second reservoir 440 can be such that the drug is mixed and/or agitated when the drug flows from the first reservoir 431 to the second reservoir 440. Thus, the drug can be reconstituted such that the particles of the drug are no longer separated.

Although FIG. 12 shows that the entire amount of the drug within the first reservoir 431 flows into the second reservoir 440, in some instances, the flow of the drug from the first reservoir 431 to the second reservoir 440 can be metered such that a desired volume of the drug is disposed within the second reservoir 440. For example, in some embodiments, the second reservoir 440 can include a volumetric indicator 446 or the like, as described above with reference to the delivery device 200 of FIGS. 5-7. In this manner, the operator can monitor the volumetric indicator 446 as the drug flows into the second reservoir 440 to ensure a desired volume of the drug that is transferred to the second reservoir 440. With the desired volume of the drug disposed in the second reservoir 440, the fluid flow path defined by the plunger 470 and/or the housing 410 can be returned to a closed configuration.

Once the desired volume of the drug is disposed within the second reservoir 440, the cartridge assembly 430 can be moved from its second configuration (FIG. 12) to its third configuration (FIG. 13) to move the delivery device 400 from the second configuration to the third configuration. For example, in some embodiments, the user can exert a force on the plunger 470 that is sufficient to move the plunger 470 from a first position relative to the second reservoir 440 (e.g., a proximal position) to a second position relative to the second reservoir 440 (e.g., a distal position), as indicated by the arrow II in FIG. 13. Therefore, with the seal member 475 forming a substantially fluidic seal with the inner surface 444 of the second reservoir 440, the distal movement of the seal member 475 exerts a pressure on a surface of the drug within the second reservoir 440 that is sufficient to expel the drug formulation through the lumen 424 of the puncture member 420. For example, in some embodiments, the pressure exerted on the surface of the drug formulation can increase the pressure within the second reservoir 440 to a pressure that is sufficient to open a valve (not shown) of the second reservoir 440 and/or of the puncture member 420 (as described above with reference to the second reservoir 340 and the puncture member 320, respectively, shown in FIGS. 8-10). In other embodiments, the increase in the pressure within the second reservoir 440 can be sufficient to break a frangible seal or the like. Thus, the delivery device 400 can deliver a desired volume of a drug formulation to the suprachoroidal space of the eye and the drug formulation can flow within the suprachoroidal space to be delivered to, for example, the posterior region of the eye.

While the delivery devices 200, 300, and 400 have been shown and described above as including a first reservoir (e.g., the first reservoirs 231, 331, and 431, respectively) and a second reservoir (e.g., the second reservoir 240, 340, and 440, respectively) that are substantially housed by a housing (e.g., the housing 210, 310, and 410, respectively), in other embodiments, a delivery device can include at least one reservoir that is disposed substantially outside of a housing. In such embodiments, however, the delivery device can include a puncture member that has a lumen with a diameter that substantially limits and/or prevents a drug formulation from being drawn from an external reservoir and into an internal reservoir, while still allowing a drug formulation to be expelled (e.g., pushed) through the lumen. In this manner, the delivery device of such embodiments can include an alternative method for drawing a drug formulation from an external reservoir and into an internal reservoir. Such embodiments can allow the use of a pre-filled container in conjunction with a delivery device.

Figure 14:
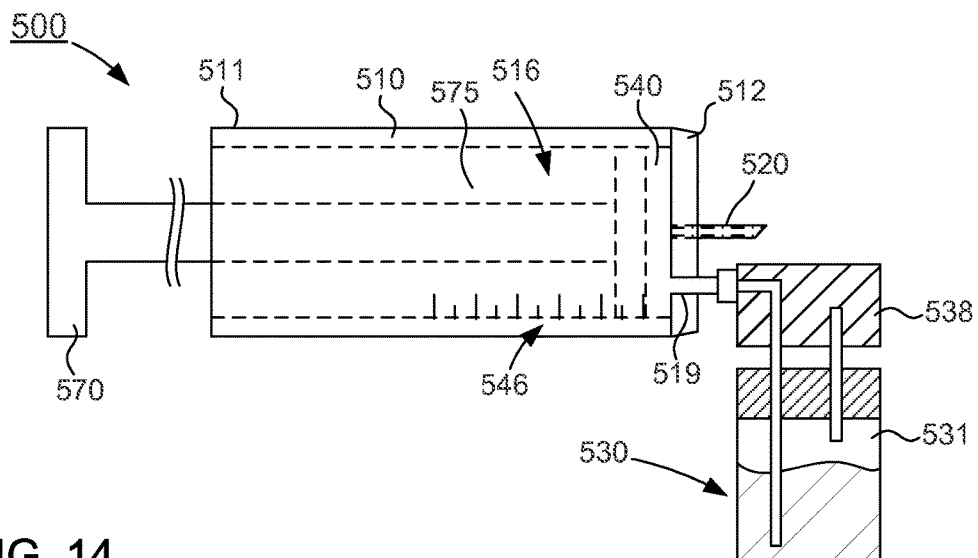
FIGS. 14-16 are schematic, illustrations of a delivery device according to an embodiment in a first configuration, a second configuration, and a third configuration, respectively.
Figure 15:
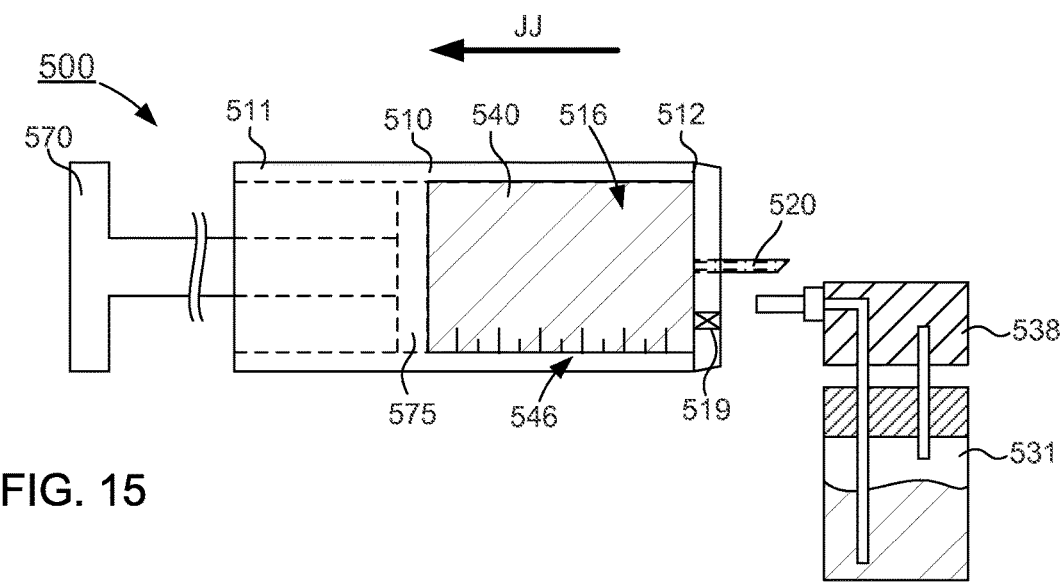
Figure 16:
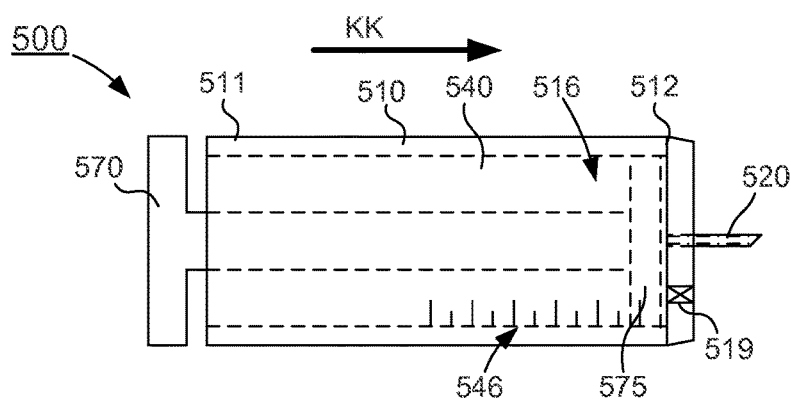

For example, FIGS. 14-16 are schematic illustrations of a delivery device 500 according to an embodiment in a first configuration, a second configuration, and a third configuration, respectively. The delivery device 500 includes a housing 510, a puncture member 520, a cartridge assembly 530, and a plunger 570. As shown in FIG. 14, the cartridge assembly 530 can be, for example, an external cartridge. The cartridge assembly 530 includes at least a first reservoir 531 and an adapter 538. The first reservoir 531 can be any suitable fluid reservoir such as, for example, a vial, a package, a pouch, and/or the like. More specifically, in some embodiments, the first reservoir 531 can be a prefilled container that can include a predetermined volume of a drug formulation. In some embodiments, the first reservoir 531 can be packaged separately and/or stored separately from the delivery device 500. In some embodiments, the first reservoir 531 can include a volumetric indicator and/or indicia. In such embodiments, a user can, for example, select a reservoir based at least in part on the volume of the drug formulation stored therein. The first reservoir 531 can contain a volume of a drug formulation such as any of the compositions described herein.

The adapter 538 of the cartridge assembly 530 is operably coupled to the first reservoir 531 and can be removably coupled to the housing 510. In some embodiments, the adapter 538 can be, for example, a cap or the like that is coupled to the first reservoir 531. In such embodiments, the adapter 538 can be fluidically coupled to the housing 510 via any suitable intervening structure such as, for example, a cannula or the like. Therefore, the adapter 538 can place the first reservoir 531 in fluid communication a portion of the housing 510, as described in further detail herein.

The puncture member 520 defines a lumen that extends through a proximal end portion and a distal end portion. The proximal end portion of the puncture member 520 is physically and fluidically coupled to the housing 510, as described in further detail herein. The distal end portion of the puncture member 520 can include, for example, a bevel or a sharpened tip that can be substantially similar to those described in the '009 PCT application, incorporated by reference above. In some embodiments, the puncture member 520 can be substantially similar to or the same as the puncture members 220, 320, and/o 420 described herein. Thus, the puncture member 520 is not described in further detail herein.

The housing 510 has a proximal end portion 511 and a distal end portion 512 and defines an inner volume 516. The distal end portion 512 is physically and fluidically coupled to the puncture member 520 to place the lumen of the puncture member 520 in fluid communication with the inner volume 516. The proximal end portion 511 movably receives the plunger 570. For example, at least a portion of the plunger 570 is inserted through an opening defined by the proximal end portion 511 of the housing 510 to movably dispose at least a portion of the plunger 570 within the inner volume 516 of the housing 510. In this manner, the plunger 570 can be moved between a first position, a second position, and a third position relative to the housing 510. Moreover, the plunger 570 includes a seal member 575 that forms a friction fit with an inner surface of the housing 510 that defines the inner volume 516. Thus, the seal member 575 and the housing 510 can form a fluidic seal that substantially isolates a portion of the inner volume 516 that is distal to the seal member 575 from a portion of the inner volume 516 that is proximal to the seal member 575. Furthermore, with the seal member 575 forming a substantially fluid tight seal with the inner surface of the housing 510, the seal member 575 of the plunger 570 and at least a portion of the housing 510 can collectively define a second reservoir 540, as described in further detail herein.

As shown in FIG. 14, the housing 510 can include a port 519 that is at least temporarily coupled to a portion of the adapter 538 of the cartridge assembly 530. For example, in some embodiments, the port 519 can be coupled to the portion of the adapter 538 via a threaded coupling, a press fit, a friction fit, a Luer Lok®, and/or any other suitable coupling. The port 519 can be moved between a first configuration (e.g., an open configuration, see FIG. 14) and a second configuration (e.g., a closed configuration, see e.g., FIG. 15) to selectively place the second reservoir 540 in fluid communication with the adapter 538. For example, the port 519 can include a valve or the like that can be moved between an open configuration and a closed configuration. Therefore, with the adapter 538 fluidically coupled to the first reservoir 531 of the cartridge assembly 530, the port 519 can selectively place the second reservoir 540 of the delivery device 500 in fluid communication with the first reservoir 531 of the cartridge assembly 530.

In use, an operator (e.g., a doctor, technician, nurse, physician, ophthalmologist, etc.) can manipulate the delivery device 500 to couple the cartridge assembly 530 thereto. For example, in some instances, the cartridge assembly 530 can be stored separately from the delivery device 500 (e.g., stored independently such that the adapter 538 is not coupled to the housing 510). In such instances, the port 519 can be in the second configuration when the delivery device 500 is stored. Thus, the sterility of the second reservoir 540 can be maintained prior to coupling the adapter 538 to the housing 510.

With the adapter 538 operably coupled to the housing 510 and the first reservoir 531, the port 519 can be in the first, open configuration, thereby placing the second reservoir 540 in fluid communication with the first reservoir 531. Once coupled, the user can manipulate the delivery device 500 by moving the plunger 570 from its first position (FIG. 14) relative to the housing 510 to its second position (FIG. 15) relative to the housing 510, as indicated by the arrow JJ in FIG. 15. The substantially fluid tight seal between the seal member 575 and the inner surface of the housing 510 can be such that the proximal movement (e.g., in the JJ direction) of the plunger 570 creates a negative pressure within the second reservoir 540. More specifically, the proximal movement of the plunger 570 increases the volume of the second reservoir 540, which, in turn, results in a negative pressure within the second reservoir 540. Therefore, with the first reservoir 531 fluidically coupled to the second reservoir 540, the negative pressure within the second reservoir 540 results in a suction force that draws at least a portion of the drug formulation from the first reservoir 531 through the adapter 538 and the port 519 to be disposed in the second reservoir 540. In this manner, the portion of the drug is conveyed into the second reservoir 540 by a path that excludes the puncture member 520.

In some instances, the flow of the drug from the first reservoir 531 to the second reservoir 540 can be metered such that a desired volume of the drug is disposed within the second reservoir 540. For example, in some embodiments, the housing 510 can include a volumetric indicator 546 or the like. More specifically, as shown in FIG. 15, the volumetric indicator 546 can be a set of markings (e.g., lines, tick marks, hash marks, dots, etc.) that can be associated with a fill volume of the second reservoir 540. In this manner, the operator can monitor the volumetric indicator 546 as the drug flows into the second reservoir 540 and, in some instances, limit the amount of the drug that is transferred to the second reservoir 540. In other instances, substantially the entire volume of the drug can flow from the first reservoir 531 to the second reservoir 540. With the desired volume of the drug formulation disposed within the second reservoir 540, the adapter 538 can be decoupled from the port 519. In this manner, the port 519 can move from the first, open configuration to the second, closed configuration, thereby moving the delivery device 500 from the first configuration (FIG. 14) to the second configuration (FIG. 15).

With the delivery device 500 in the second configuration, the operator can manipulate the delivery device 500 to insert the puncture member 520 into, for example, ocular tissue. In some embodiments, the length of the puncture member 520 can at least partially correspond with the ocular tissue such that when inserted into the eye, the distal end portion 522 of the puncture member 520 is disposed within the suprachoroidal space and the lumen is placed in fluid communication therewith. More specifically, the distal end portion 522 of the puncture member 520 pierces the sclera of the eye and is disposed within the sclera and/or the suprachoroidal space without substantially piercing the choroid of the eye (see e.g., FIG. 1 for anatomical context).

Once the puncture member 520 is disposed within the target ocular tissue, the delivery device 500 can be moved from the second configuration (FIG. 15) to the third configuration (FIG. 16). For example, the user can exert a force on the plunger 570 to move the plunger 570 from its second position relative to the housing 510 to its third position relative to the housing 510, as indicated by the arrow KK in FIG. 16. With the lumen of the puncture member 520 in fluid communication with the second reservoir 540 and with the port 519 in the second, closed configuration, the distal movement (e.g., in the KK direction) of the plunger 570 from its second position to its third position expels the drug formulation (contained within the second reservoir 540, as described above) through the lumen of the puncture member 520. Thus, the delivery device 500 can deliver a desired volume of a drug formulation to the suprachoroidal space of the eye and the drug formulation can flow within the suprachoroidal space to be delivered to, for example, the posterior region of the eye.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and alloys thereof. The polymer may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chiorosulphonate polyolefins, polyethylene oxide, blends and copolymers thereof.

As described above, the puncture members 220, 320, 420, and 520, can be, for example, microneedles. Such microneedles can be fabricated by a variety of methods. For example, in some embodiments, the hollow microneedle, is fabricated using a laser or similar optical energy source. In one example, a microcannula may be cut using a laser to represent the desired microneedle length. The laser may also be use to shape single or multiple tip openings. Single or multiple cuts may be performed on a single microncannula to shape the desired microneedle structure, in one example, the microcannula may be made of metal such as stainless steel and cut using a laser with a wavelength in the infrared region of the light spectrum (0.7-300 μm). Further refinement may be performed using metal electropolishing techniques familiar to those in the field. In another embodiment, the microneedle length and optional bevel is formed by a physical grinding process, which for example may include grinding a metal cannula against a moving abrasive surface. The fabrication process may further include precision grinding, micro-bead jet blasting and ultrasonic cleaning to form the shape of the desired precise tip of the microneedle.

A wide range of ocular diseases and disorders may be treated by the methods and devices described herein. Non-limiting examples of ocular diseases include uveitis, glaucoma, diabetic macular edema or retinopathy, macular degeneration, retinoblastoma, and genetic diseases. The methods described herein are particularly useful for the local delivery of drugs that need to be administered to the posterior region of the eye, for example the retinochoroidal tissue, macula, and optic nerve in the posterior segment of the eye. In one embodiment, the delivery methods and devices described herein may be used in gene-based therapy applications. For example, the methods may administer a fluid drug formulation into the suprachoroidal space to deliver select DNA, RNA, or oligonucleotides to targeted ocular tissues, The microneedles can be used to target delivery to specific tissues or regions within the eye or in neighboring tissue. In various embodiments, the methods may be designed for drug delivery specifically to the sclera, the choroid, the Bruch's membrane, the retinal pigment epithelium, the subretinal space, the retina, the macula, the optic disk, the optic nerve, the ciliary body, the trabecular meshwork, the aqueous humor, the vitreous humor, and other ocular tissue or neighboring tissue in need of treatment.

A wide range of drugs may be formulated for delivery to ocular tissues using the present systems and devices described herein. Moreover, any of the delivery devices and/or methods described herein can involve, include and/or contain any of the drugs described herein. For example, in some embodiments, the medicament containment chamber 1310, 2310, 3310, or any other medicament containment chamber can contain any of the drugs and/or formulations described herein. As used herein, the term "drug" refers to any prophylactic, therapeutic, or diagnostic agent (e.g., a contrast agent). The drug may be selected from suitable proteins, peptides and fragments thereof, which can be naturally occurring, synthesized or recombinantly produced. Representative examples of types of drugs for delivery to ocular tissues include antibodies, anti-viral agents, chemotherapeutic agents (e.g., topoisomerase inhibitors), analgesics, anesthetics, aptamers, antihistamines, anti-inflammatory agents, and anti-neoplastic agents. In one embodiment, the drug is triamcinolone or triamcinolone acetonide.

The term "antibody" is intended to refer broadly to any immunologic binding agent such as IgG, IgM, IgA, IgD and IgE. An antibody can be monoclonal or polyclonal, and in one embodiment, is a humanized antibody. The term "antibody" is also used to refer to any antibody-like molecule that has an antigen binding region, and includes antibody fragments such as Fab', Fab, $F(ab')^2$, single domain antibodies (DABs), Fv, scFv (single chain Fv), and engineering multivalent antibody fragments such as dibodies, tribodies and multibodies. The techniques for preparing and using various antibody-based constructs and fragments are well known in the art (see, e.g., Antibodies: A Laboratory Manual, Cold Spring Harbor Laboratory, 1988; incorporated herein by reference).

Non-limiting examples of specific drugs and classes of drugs include β-adrenoceptor antagonists (e.g., carteolol, cetamolol, hetaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), topoisomerase inhibitors (e.g., topotecan, irinotecan, camptothecin, lamellarin D, etoposide, teniposide, doxorubicin, mitoxantrone, amsacrine), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegagtanib sodium, ranibizumab, aflibercept and bevacizumab.

In one embodiment, the drug is an integrin antagonist, a selectin antagonist, an adhesion molecule antagonist (e.g., intercellular adhesion molecule (ICAM)-1, ICAM-2, ICAM-3, platelet endothelial adhesion molecule (PCAM), vascular cell adhesion molecule (VCAM)), a leukocyte adhesion-inducing cytokine or growth factor antagonist (e.g., tumor necrosis factor-α (TNF-α), interleukin-1β (IL-1β), monocyte chemotactic protein-1 (MCP-1), or a vascular endothelial growth factor (VEGF)). In some embodiments, a vascular endothelial growth factor (VEGF) inhibitor is administered with one of the microneedles described herein. In some embodiments, two drugs are delivered by the methods described herein. The compounds may be administered in one formulation, or administered serially, in two separate formulations. For example, both a VEGF inhibitor and VEGF are provided. In some embodiments, the VEGF inhibitor is an antibody, for example a humanized monoclonal antibody. In further embodiments, the VEGF antibody is bevacizumab. In another embodiment, the VEGF inhibitor is ranibizumab, aflibercept or pegaptanib. In still other embodiments, the devices and methods described herein can be used to deliver one or more of the following VEGF antagonists: AL8326, 2C3 antibody, AT001 antibody, HyBEV, bevacizumab (Avastin), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, Sutent (sunitinib malate), INDUS815C, R84 antibody, KD019, NN3, allogenic mesenchymal precursor cells combined with an anti-VEGF agent or antibody, MGCD265, MG516, VEGF-Receptor kinase inhibitors, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble Flt1 receptor, Cediranib (Recentin), AV-951 (Tivozanib, KRN-951), Stivarga (regorafenib), Volasertib (BI6727), CEP11981, KH903, Lenvatinib (E7080), terameprocol (EM1421), ranibizumab (Lucentis), Votrient (pazopanib hydrochloride), PF00337210, PRS050, SP01 (curcumin), Carboxyamidotrazole orotate, hydroxychloroquine, linifanib (ABT869, RG 3635), Iluvien (fluocinolone acetonide), ALG1001, AGN150998, DARPin MP0112, AMG386, ponatinib (AP24534), AVA101, Vargatef (nintedanib), BMS690514, KH902, golvatinib (E7050), Afinitor (everolimus), Dovitinib lactate (TKI258, CHIR258), ORA101, ORA102, Axitinib (inlyta, AG013736), Plitidepsin (Aplidin), Lenvatinib mesylate, PTC299, aflibercept (Zaltrap, Eylea), pegaptanib sodium (Macugen, LI900015), Visudyne (verteporfin), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (Y2T968D1), and AL3818. In addition, delivery of a VEGF inhibitor or VEGF antagonist using the microneedle devices and methods disclosed herein may be combined with one or more agents listed herein or with other agents known in the art.

In one embodiment, delivery of a VEGF antagonist to the suprachoroidal space of the eye using the devices and methods disclosed herein is used to treat, prevent and/or ameliorate a disease or disorder selected from leukemia, relapsed/refractory leukemia, acute lymphoblastic leukemia, Acute myelogenous leukemia, relapsed or refractory acute myeloid leukemia, atopic dermatitis, recurrent or metastatic carcinoma of the urothelium, advanced urothelial carcinoma, blood disorders, myelofibrosis, brain tumor, glioblastoma, glioma, meningioma, cancer, carcinomatous meningitis (neoplastic meningitis), choroidal neovascularization (CNV), subfoveal choroidal neovascularization, chronic lymphocytic leukemia, chronic myelogenous leukemia, refractory chronic myelogenous leukemia, colon cancer, colorectal cancer, degenerative nerve diseases, Neurodegenerative diseases, diabetic macular edema, visual Impairment due to diabetic macular edema, diabetic retinopathy, dry eye syndrome (inflammation and corneal tissue damage of dry Eye), endometrial cancer, eye diseases, ocular diseases, ocular neovascularization, eye cancer, Neurofibromatosis Type II, head and neck cancer, hematological malignancies, Kaposi's Sarcoma, Hepatocellular Carcinoma, Lung cancer, macular degeneration, age related macular degeneration, exudative age-related macular degeneration, neovascular (wet) age-related macular degeneration (AMD)), subfoveal Neovascular Age-Related macular degeneration, macular edema, macular edema associated with Branch Retinal Vein Occlusion, macular edema following retinal vein occlusion, macular edema with Retinal Vein Occlusion (RVO), multiple myeloma, relapsed or refractory multiple myeloma, multiple sclerosis, myopia, pathological myopia, neuroendocrine tumor, carcinoid tumor, neuroendocrine tumor, non-Hodgkin's Lymphoma, Diffuse Large B-Cell Lymphoma, Non-Small-Cell Lung cancer, Non-Squamous Non-Small-Cell Lung cancer, Non-small-cell--lung Adenocarcinoma, Squamous Non-Small-Cell Lung cancer, corneal graft rejection, osteoarthritis, recurrent symptomatic malignant ascites, peripheral T-cell lymphoma, androgen Independent Psoriasis, pulmonary Fibrosis, Idiopathic Pulmonary Fibrosis, respiratory diseases, retinal detachment, retinal disorders, retinitis pigmentosa, retinal vein occlusion, branch retinal vein occlusion, central retinal vein occlusion, rheumatoid arthritis, sarcoma, alveolar soft part sarcoma, soft tissue sarcoma, scleroderma/systemic sclerosis, solid tumors, refractory germ cell tumors, thyroid cancer, differentiated or medullar thyroid cancer, and West Syndrome (Infantile Spasm).

In certain embodiments, the drug delivered to the suprachoroidal space using the devices and methods disclosed herein is rapamycin (Sirolimus, Rapamune). In one embodiment, the devices (e.g., microneedle devices) and methods disclosed herein are used in conjunction with rapamycin to treat, prevent and/or ameliorate a wide range of diseases or disorders including, but not limited to: abdominal neoplasms, acquired immunodeficiency syndrome, acute coronary syndrome, acute lymphoblastic leukemia, acute myelocytic leukemia, acute non-lymphoblastic leukemia, adenocarcinoma, adenoma, adenomyoepithelioma, adnexal diseases, anaplastic astrocytoma, anaplastic large cell lymphoma, anaplastic plasmacytoma, anemia, angina pectoris, angioimmunoblastic lymphadenopathy with dysproteinemia, angiomyolipoma, arterial occlusive diseases, arteriosclerosis, astrocytoma, atherosclerosis, autoimmune diseases, B-cell lymphomas, blood coagulation disorders, blood protein disorders, bone cancer, bone marrow diseases, brain diseases, brain neoplasms, breast beoplasms, bronchial neoplasms, carcinoid syndrome, carcinoid Tumor, carcinoma, squamous cell carcinoma, central nervous system diseases, central nervous system neoplasms, choroid diseases, choroid plexus neoplasms, choroidal neovascularization, choroiditis, chronic lymphocytic leukemia, chronic myeloid leukemia, chronic myelomonocytic leukemia, chronic myeloproliferative disorders, chronic neutrophilic leukemia, clear cell renal cell carcinoma, colonic diseases, colonic neoplasms, colorectal neoplasms, coronary artery disease, coronary disease, coronary Occlusion, coronary restenosis, coronary stenosis, coronary thrombosis, cutaneous T-cell lymphoma, diabetes mellitus, digestive system neoplasms, dry eye syndromes, ear diseases, edema, endocrine gland neoplasms, endocrine system diseases, endometrial neoplasms, Endometrial stromal tumors, Ewing's sarcoma, exanthema, eye neoplasms, fibrosis, follicular lymphoma, gastrointestinal diseases, gastrointestinal neoplasms, genital neoplasms, glioblastoma, glioma, gliosarcoma, graft vs host disease, hematologic diseases, hematologic neoplasms, hemorrhagic disorders, hemostatic disorders, Hodgkin disease, Hodgkin lymphoma, homologous wasting disease, immunoblastic lymphadenopathy, immunologic deficiency syndromes, immunoproliferative disorders, infarction, inflammation, intestinal diseases, intestinal neoplasms, ischemia, kidney cancer, kidney diseases, kidney neoplasms, leukemia, B-Cell, leukemia, lymphoid, liver cancer, liver diseases, lung diseases, lymphatic diseases, lymphoblastic lymphoma, lymphoma, macular degeneration, macular edema, melanoma, mouth neoplasms, multiple myeloma, myelodysplastic syndromes, myelofibrosis, myeloproliferative disorders, neuroectodermal tumors, neuroendocrine tumors, neuroepithelioma, neurofibroma, renal cancer, respiratory tract diseases, retinal degeneration, retinal diseases, retinal neoplasms, retinoblastoma, rhabdomyosarcoma, thoracic neoplasms, uveitis, vascular diseases, Waldenstrom Macroglobulinemia, and wet macular degeneration. In addition, delivery of rapamycin using the microneedle devices and methods disclosed herein may be combined with one or more agents listed herein or with other agents known in the art.

In one embodiment, the drug delivered to ocular tissue, for example the sclera or suprachoroidal space, using the microneedle devices and methods disclosed herein reduces, inhibits, prevents and/or ameliorates inflammation. Examples of drugs that reduce, inhibit, prevent and/or ameliorate inflammation include (but are not limited to): 19AV Agonists, 19GJ agonists, 2MD Analogs, 4SC101, 4SC102, 57-57, 5-HT2 Receptor Antagonist, 64G12, A804598, A967079, AAD2004, AB1010, AB224050, abatacept, Abegrin, Abevac, AbGn134, AbGn168, Abki, ABN912, ABR215062, ABR224050, Abrammune, Abreva, ABS15, ABS4, ABS6, ABT122, ABT325, ABT494, ABT874, ABT963, ABXIL8, ABXRB2, AC430, Accenetra, Acdeam, ACE772, Acebid, Acebloc, aceclofenac, acetaminophen, chlorzoxazone, serrapeptase, tizanidine hydrochloride, betadex, Aceclogesic Plus, Aceclon, Acecloren, Aceclorism, acecrona, Aceffein, acemetacin, Acenac, Acenterine. Acetal-SP, ibuprofen, Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Aethelea liofilizado, Actifast, Actimab-B, Actiquim, Actirin, Actis PLUS, activated leukocyte cell adhesion molecule antibody, Acular X, AD452, adahi-mumab, ADAMTS5 Inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwifiam, AEB071, Aetnal, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzumab, Alequel, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, Alpha-1-antitrypsin, Alpha2Betal Integrin Inhibitors, Alphacort, Alphafen, alphahexidine, alpha-trypsin, Alphintern, Alpinamed mobility omega 3, Alpox AL-Rev1, Alterase, ALX0061, ALX0761, ALXN1007, ALXN 1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, Amifenac, Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA, Anflene, ANG797, Anilixin, Anmerushin, Annexin 1 peptides, annexin A5, Anodyne, Ansaid, Anspirin, Antarene, Anti BST2 antibody, Anti C5a MAb, Anti ILT7 antibody, Anti VLA1 antibodyAnti-alpha11 antibody, Anti-CD4 802-2, Anti-CD86 Monoclonal Antibody, Anti-chemokine, Anti-DC-SIGN, Anti-HMGB-1 MAb, Anti-IL-18 Mab, Anti-IL-1R MAb, Anti-1L-1R MAb, Anti-IL23 BRISTOL, Anti-inflammatory Peptides, Anti-interleukin 1Beta antibody, Anti-LIGHT antibody, Anti-LIGHT antibody, Anti-MIF Antibody, Anti-MIF Antibody, Anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazorie, APD334, Apentac, APG103, Apidone, apilimod mesylate, Apitac, Apitoxin, Apizel, APN Inhibitor, apo-Azathioprine, Apo-Dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, Arthrovas, Artifit, Artigo, Artin, Artinor, Artisid, Artoflex, Artren Hipergel, Artridol, Artrilase, Artrocaptin, Artrodict, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, aspirin, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATI003, atiprimod, ATL1222, ATN103, ATN192, ATR107, Atri, Armin, Atrosab antibody, ATX3105, AU801, auranofin, Aurobin, Auropan, Aurothiu, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azaeortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenae, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, B1695500, B1695501, B1A12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BR02001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bucot, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, candida albicans antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, CaspaCIDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 Antagonist, CCR6 Inhibitor, CCR7 Antagonist, CCRL2 antagonist, CCX025, CCX354, CCX634, CD Diclofenac, CD102, CD103 Antibody, CD103 Antibody, CD137 antibody, CD16 antibody, CD18 antibody, CD 19 antibody, CD1d Antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP87O, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CeliCept, Cellmune, Celosti, Celoxib, Ceiprot, Cekidex, cenicriviroc mesylate, cenplacel-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN 15051, CGEN15091, CGEN25017, COEN25068, CGEN40, CGEN54, CGEN768, CGEN855, CGI1746, CGI560, CGI676, Cgtx-Peptides, CH1504, CH4051, CH4446, chaperonin 10, chemokine C-C motif ligand 2, chemokine C-C motif ligand 2 antibody, chemokine C-C motif ligand 5 antibody, chemokine C-C motif receptor 2 antibody, chemokine C-C motif receptor 4 antibody, chemokine C-X-C motif ligand 10 antibody, chemokine C-X-C motif ligand 12 aptamer, Chemotaxis Inhibitor, Chillmetacin, chitinase 3-like 1, Chlocodemin, Chlorquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cionoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CNDO201, CNI1493, CNTO136, CNTO148, CNTO1959, Cobefen, CoBenCoDerm, Cobix, Cofenac, Cofenac, COG241, COL179, colchicine, Colchicum Dispert, Colchimax, Colcibra, Coledes A, Colesol, Colifoam, Colirest, collagen, type V, Comcort, complement component (3b/4b) receptor 1, Complement Component C1s Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Curtain. Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM Ion Channel inhibitor, Cratisone, CRB15, CRC4273, CRC4342, C-reactive protein 2-methoxyethyl phosphorothioate oligonucleotide, Crea Vax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrin CLARIS, CYT007TNFQb, CYT013IL1bQb, CYT015IL17Qb, CYT020TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declopher3, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone, Deltacortril, Deltafluorene, Deltaslone, Deltasone, Deltastab, Deltonin, Demarin, Demisone, Denebola, denileukin diftitax, denosumab, Denzo, Depocortin, Depomedrol, Depomethotrexate, Depopred, Deposet, Depyrin, Derinase, Dermol, Dermolar, Dermonate, Dermosone, Dersone, Desketo, desonide, desoxycorticosterone acetate, Deswon, Dexa, Dexabene, Dexacip, Dexacort, Dexacortisone, Dexaeotisil, Dexadic, Dexadrin, Dexadron, Dexafar, Dexahil, Dexalab, Dexalaf, Dexalet, Dexalgen, Dexallion, Dexalocal, Dexalone, Dexo-M, Dexamecortin, Dexamed, Dexamedis, Dexameral, Dexameta, Dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexorty, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Dielogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Dolofit, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, EC0286, EC0565, EC0746, Ecax, *echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, elF5A1 siRNA, Ekarzin, elafin, Eldoflam, Elidel, Eliflam, Elisone, Elmes, Ehnetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra. Feverlet, Extrapan, Extrauma, Exudase, F16, F991, Faleant, Falzy, Farbovil, Farcometbacin, Farnerate, Farnezone, Farnezone, Farotrin, fas antibody, Fastflam, FasTRACK, Fastum, Fauldmetro, FcgammaRIA antibody, FE301, Febrofen, Febrofid, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flarizen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquirt, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemmer, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hCG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, IBuscent, Ibusoft, Ibusuki Penjeong, Ibususpen, Ibutard, Ibutop, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Immoral, Immodin, IMMU103, IMMU106, Immucept, Immufine, Immunex Syrup, immunogiubulin, immunoglobulin G, Immunoprin, ImmunoRel, Immurin, IMO8400, IMP731 antibody, Implanta, imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, indomethasone, Indometin, indomin, Indopal, Indoron, Indotroxirt, INDUS830, INDUS83030, Infladase, Infalmac, Inflammasome inhibitor, Inflavis, Inflaxen, Inflectra, infliximab, Ingalipt, Inicox dp, Inmecin, Inmunoartro, Innamit, InnoD06006, INO7997, Inocin, Inoten, Inovan, Inpra, Inside Pap, Insider-P, instacyl, Instracool, Intafenac, Intaflam, Inteban, Intehan Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, lomab B, IOR-T3, IP751, IPH2201, IPH2301, IPH24, IPH33, IPHI45, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IW001, Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketones, Ketoplus Kata Plasma, ketoprofen, Ketones, Ketorin, ketorolac, ketorolac tromethamine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40or, KLS-40ra, KM277, Knavon, Kodolo orahase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv 1.3 Blocker, Kv1.3 4SC, Kv1.3 inhibitor, KVK702, Kynol, L156602, Labizone, Labohydro, Lahopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LeritiRA, LEO15520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafiuo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lorncrat, lornoxicam, Lorox, losinapimod, loteprednol etabonate, Loteprednol, Lotirac, Low Molecular Ganoderma Lucidum Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxy12, Maxy30, MAXY4, Maxy735, Maxy740, Mayfenamic, MB11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melujin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHS class II beta chain peptide, Micar, Miclofen, Miclofenac, Micofenolato Mofetil, Micosone, Microdase, micro RNA 181a-2 oligonucleotide, MIF Inhibitors, MIFQh, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alphaluminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Musliax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Nakiofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Napox, naproxen, naproxen sodium, Naproxin, Napozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, NewGam, Newmafen, Newmatal, Newsicam, NEX1285, sFcRIIB, Nextomab, NF-kappaB Inhibitor, NE-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nitimat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCS5, NPRCS6, NPS3, NPS4, nPTery, NU3450, nuclear factor NF-kappa-B p65 subunit oligonucleotide, Nucort, Nulojix, Numed-Plus, Nurokind Ortho, Nusone-H, Nutrikemia, Nuvion, NV07alpha, NX001, Nycelobate, Nyox, Nysa, Obarcort, OC002417, OC2286, ocaratuzumab, OCTSG815, Oedemase, Oedemase-D, ofatumumab, Ofgyl-O, Ofvista, OHR118, OKi, Okifen, Oksamen, Olai, olokizmnab, Omeprose E, Omnacortil, Omneed, Omniclor, Omnigel, Omniwel, onercept, ONO4057, ONS1210, ONS1220, Ontac Plus, Ontak, ONX0914, OPC6535, opebacan, OPN101, OPN201, OPN302, OPN305, OPN401, opreivekin, OPT66, Optifer, Opfiflur, OptiMIRA, Orabase Hea, Oradexon, Oraflex, Oral-Fenac, Oralog, Oralpred, Ora-sed, Orasone, orBec, Orbone forte, Ord, ORE10002, ORE10002, Orencia, Org214007, Org217993, Org219517, Org223119, Org37663, Og39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Ostehte, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha inhibitor, p38 Antagonist, p38 MAP kinase inhibitor, p38alpha MAP Kinase inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentaigin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PH5, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractain, Pircxyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygom S/D, Polyphlogin, Poncif, Ponstan, Ponstil Forte, Porine-A Neoral, Potaba, potassium aminobenzoate, Potencort, Povidone, povidone iodine, pralnacasan, Prandin, Prehel, Precodil, Precortisyl Forte, Precortyl, Predfoam, Predicort, Predicorten, Predilab, Predilone, Predmetil, Predmix, Predna, Prednesol, Predni, prednicarbate, Prednicort, Predindib, Prednifarma, Prednilasca, prednisolone, prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Propopnol, propyl nicotinate, Prostaloc, Prostapol, Protacin, Protase, Protease Iinhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Planninq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix Isatidis, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade, Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ1445380, RX10001, Rycloser MR, Rydol, S1P Receptor Agonists, S1P Receptor Modulators, S1P1 Agonist, S1P1 receptor agonist, S2474, S3013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SB1087, SC080036, SC12267, SC409, Scaflam, SCD ketoprofen, SCIO323, SCIO469, SD-15, SD281, SDP051 antibody, Sd-rxRNA, secukinumab, Sedase, Sedilax, Sefdene, Seizyme SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, SI615, SI636, Sigmasporin, Sigmasporin, SIM916, Simpone, Simulect, Sinacort, Sinalgia, Sinapol, Sirtatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SNO030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550 Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSS07 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Sterio, Sterisone, Steron, stichodactyla helianthus peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarmac, tarenflurbil, Tarimus, Tarproxen, Tauxib, Tazomust, TBR652, TC5619, T-cell, immune regulator 1. ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypeptides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamily1B oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767 Uremol-HC, Urigon, U-Ritis, ustekinumab, V85546, Valcib, Valcox, vaidecoxib, Valdez, Vaidixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, Venimmun N, Venoforte, Venoglobulin-IH, Venozel, Veral, Verax, vercirnon, vero-Dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab. Votan-SR, VR909, VRA002, VRP1008, VRS826, VRS826, VT111, VT214, VT224, VT310, VT346, VT362, VTX763, Vurdon, VX30 antibody, VX467, VX5, VX509, VX702, VX740, VX745, VX745, VX850, W54011, Walacort, Walix, WC3027, Wilgraf, Winfiam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XToll, Xtra, Xylex-H, Xynofen SR, Yang Shu-IVTG, YHB14112, YM974, Youfeline, Youfenac, Yuma, Yumerol, Yuroben, YY piroxicam, Z104657A, Zacy, Zaltokin, zaltoprofen, Zap70 inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte in addition, the anti-inflammatory drugs, as listed above, may be combined with one or more agents listed above or herein or with other agents known in the art.

In one embodiment, a drug that reduces, inhibits, prevents and/or ameliorates inflammation, for example, one of the drugs provided above, is delivered to the suprachoroidal space of the eye using the microneedle devices and methods disclosed herein, and is used to treat, prevent and/or ameliorate a disease or disorder selected from arthritis, degenerative arthritis, psoriatic arthritis, arthritic disorders, arthritic pain, arthrosis, autoimmune arthritis, autoimmune diseases, autoimmune disorders, axial spondyloarthritis, chronic prosthetic joint infection, collagen induced arthritis, osteoarthritis, rheumatoid arthritis, senile arthritis, seronegative oligoarthritis of the knee, allergic and autoimmune inflammatory diseases, inflammatory diseases, inflammatory disorders, collagen diseases, discoid Lupus Erythematosus, immune deficiencies, immune diseases, immune disorders, immunodeficiency diseases, immunodeficiency disorders, immunoglobulin (IgG2) deficiency, immunoglobulin deficiency, Inflammation, Lambert-Eaton myasthenia syndrome, polymyositis, dermatomyositis, polyneuritis, post-operative ocular inflammation, polychondritis, sporadic inclusion body myositis, Systemic Lupus Erythematosus, T cell deficiency, TNF-receptor associated periodic syndrome, tropical spastic paraparesis, Wegener Granulomatosis, X-linked severe combined immunodeficiency disease, Behcet's disease, Crohn's disease, Crohn's Fistula, cutaneous Lupus Erythematosus, acute inflammation, acute inflammatory edema, adrenocortical insufficiency, cerebral inflammation, chronic lung inflammation, corticoid-responsive inflammatory skin disorders, cutaneous inflammation, dermal inflammation, dry skin inflammatory disease, ear edema, ear inflammation, glossitis, inflammatory bowel disease, inflammatory degenerative disease, inflammatory disorders of the eye and/or ear, inflammatory lesions in fungal infections, inflammatory lesions, inflammatory pain, inflammatory skin diseases or disorders, mouth and gum inflammation, mouth and throat inflammation, musculoskeletal disorders, otitis, pelvic inflammatory disease, perianal inflammation, post operative inflammation, pulmonary inflammation, rectal inflammation, refractory idiopathic inflammatory myopathies, seborrhoeic dermatitis, aphthous ulcerations, chronic polyarthritis, juvenile rheumatoid arthritis, rheumatic diseases, Sjogren's syndrome, opthaimic for Sjogren's syndrome, transplant rejection, acute allograft rejection, chronic graft rejection, graft versus host disease, humoral rejection in heart transplantation, humoral rejection in kidney transplantation, organ rejection in renal transplantation, solid organ transplant rejection, bronchiolitis obliterans after lung transplantation, rejection of bone marrow transplant, chronic lung transplant rejection, Corneal graft rejection, delayed graft function in kidney transplantation, heart transplant rejection, Homotransplantation rejection, immune rejection of hESC-derived therapeutic grafts, kidney transplant rejection, liver transplant rejection, lung transplant rejection, organ rejection, pancreatic islet transplantation rejection in type I diabetes, renal transplant rejection and xenograft rejection.

In one embodiment, the drug delivered to the suprachoroidal space using the microneedle devices and methods disclosed herein treats, prevents, and/or ameliorates macular degeneration (e.g., age related macular degeneration, dry age related macular degeneration, exudative age-related macular degeneration, geographic atrophy associated with age related macular degeneration, neow.scular (wet) age-related macular degeneration, neovascular maculopathy and age related macular degeneration, occult with no classic choroidal neovascularization (CNV) in age-related macular degeneration. Stargardt's disease, Subfoveal wet Age-Related macular degeneration, and Vitreomacular Adhesion (VMA) associated with Neovascular Age Related macular degeneration). Examples of drugs that treat, prevent and/or ameliorate macular degeneration that can be used in conjunction with the devices and methods described herein include, but are not limited to: A0003, A36 peptide, AAV2-sFLT01 , ACE041, ACU02, ACU3223, ACU4429, AdPEDF, aflibecept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, sub-family A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNTO2476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD45145, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with Lucentis, iCo-008, Icon1, I-Gold, Ilaris, Iluvien, Iluvien with Lucentis, immunoglobulins, integrin alpha5beta1 immunoglobulin fragments, integrin inhibitor, IRIS Lutein, 1-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with myrtillus extract, Lutein with zeaxanthin, M200, M200 with Lucentis. Macugen, MC1101, MCT355, mecamylamine, Microplasmin, motexafin lutetium, MP0112, NADPH oxidase inhibitors, Neoretna, neuotrophin 4 gene, Nova21012, Nova21013, NT501, NT503, Nutri-Stulln, ocriplasmin, OcuXan, Oftan Macula, Optrin, ORA102 with Avastin, P144, P17, Palomid 529, PAN90806, Panzem, Panzem, PARP Inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005,PMX53, POT4, PRS055, PTK787, ranibizumab, ranibizumab with triamcinolone acetonide, ranibizumab with verteporfin, ranibizumab with volociximab, RD27, Rescula, Retaane, retinal pigment epithelial cells, RetinoStat, RG7417, RN6G, RT101, RTU007, SB267268, serpin peptidase inhibitor, clade F, member 1 gene, shark cartilage extract, Shef1, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TKI, TLCx99, TRC093, TRC105, triamcinolone acetonide with verteporfin, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF Inhibitor, verteporfin, Visudyne, Visudyne with Lucentis and dexamethasone, Visudyne with triamcinolone acetonide, Vivis, volociximab, Votrient, XV615, zeaxanthin, ZFP TF, zinc-mortocysteine and Zybrestat. In one embodiment, one or more of the macular degeneration treating drugs described above is combined with one or more agents listed above or herein or with other agents known in the art.

In one embodiment, the methods and devices provided hererin are used to delivery triamcinolone or triamcinolone acetonide to the suprachoroidal space of an eye of a patient in need thereof. In a further embodiment, the triamcinolone or triamcinolone acetonide is delivered for the treatment of sympathetic ophthalmia, temporal arteritis, uveitis and/or ocular inflammatory conditions. In one embodiment, triamcinolone car triamcinolone acetonide is delivered to the suprachoroidal space of the eye in a patient in need of treatment of sympathetic opthalmia with the methods and devices described herein. In another embodiment, triamcinolone or triamcinolone acetonide is delivered to the suprachoroidal space of the eye in a patient in need of treatment of temporal arteritis with the methods and devices described herein. In yet another embodiment, triamcinolone or triamcinolone acetonide is delivered to the suprachoroidal space of the eye in a patient in need of treatment of uveitis, with the methods and devices described herein. In another embodiment, triamcinolone or triamcinolone acetonide is delivered to the suprachoroidal space of the eye in a patient in need of treatment of one or more ocular inflammatory conditions, with the methods and devices described herein.

The triamcinolone composition provided herein, in one embodiment, is a suspension comprising microparticles or nanoparticles of triamcinolone or triamcinolone acetonide. The microparticies, in one embodiment, have a $D_{50}$ of about 3 μm or less. In a further embodiment, the $D_{50}$ is about 2 μm. In another embodiment, the $D_{50}$ is about 2 μm or less. In even another embodiment, the $D_{50}$ is about 1000 nm or less. The micropardcles, in one embodiment, have a $D_{99}$ of about 10 μm or less. In another embodiment, the $D_{99}$ is about 10 μm. In another embodiment, the $D_{99}$ is less than about 10 μm or less than about 9 μm or less.

In one embodiment, the triamcinolone composition comprises triamcinolone microparticles. In a further embodiment, the composition comprises polysorbate 80. In another embodiment, the triamcinolone composition comprises one or more of $CaCl_2$, $MgCl_2$, sodium acetate and sodium citrate. In one embodiment, the composition comprises polysorbate 80 at a w/v% of 0.02% or about 0.02%, 0.015% or about 0.015%.

In certain embodiments the drug delivered to ocular tissues using the microneedle devices and methods disclosed herein treats, prevents, and/or ameliorates fibrosis (e.g. myelofibrosis, fibrosis in diabetic nephropathy, cystic fibrosis, scarring, and skin fibrosis).

In one embodiment, a drug that treats, prevents and/or ameliorates fibrosis is used in conjunction with the devices and methods described herein, and is delivered to the suprachoroidal space of the eye. In a further embodiment, the drug is Actimmune with Pirfenidone, ACUHTR028, AlphaVBeta5, amiaobenzoate potassium, amyloid P, ANG1122, ANG1170, ANG3062, ANG3281, ANG3298, ANG4011, Anti-CTGF RNAi, Aplidin, astragalus membranaceus extract with salvia and schisandra densis, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RX1109, secretin, STX100, TGF-beta Inhibitor, transforming growth factor, beta receptor 2 oligonucleotide, VA999260 or XV615. In one embodiment, one or more of the fibrosis treating dugs described above is combined with one or more agents listed above or herein or with other agents known in the art.

In one embodiment, a drug that treats, prevents and/or ameliorates diabetic macular edema is used in conjunction with the devices and methods described herein, and is delivered to the suprachoroidal space of the eye. In a further embodiment, the drug is AKB9778, bevasiranib sodium, Cand5, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0S03 or TiLipix. In one embodiment, one or more of the diabetic macular edema treating drugs described above is combined with one or more agents listed above or herein or with other agents known in the art.

In one embodiment, a drug that treats, prevents and/or ameliorates macular edema is used in conjunction with the devices and methods described herein, and is delivered to the suprachoroidal space of the eye. In a further embodiment, the drug is denufosol tetrasodium, dexamethasone, ecallantide, pegaptanib sodium, ranibizumab or triamcinolone. In addition, the drugs delivered to ocular tissues using the microneedle devices and methods disclosed herein which treat, prevent, and/or ameliorate macular edema, as listed above, may be combined with one or more agents listed above or herein or with other agents known in the art.

In one embodiment, a drug that treats, prevents and/or ameliorates ocular hypertension is used in conjunction with the devices and methods described herein and is delivered to the suprachoroidal space of the eye. In a further embodiment, the drug is 2-MeS-beta ganrma-CC12-ATP, Aceta Diazol, acetazolamide, Aristomol, Arteoptic, AZD4017, Betaimic, betaxolol hydrochloride, Betimol, Betoptic S, Brimodin, Bimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortinol, Glaumol, Hypadil, Ismotic, isopropyl unoprostone, isosorbide, Latalux, latanopost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to ocular tissues using the microneedle devices and methods disclosed herein which treat, prevent, and/or ameliorate ocular hypertension, as listed above, may be combined with one or more agents listed above or herein or with other agents known in the art.

In certain embodiments one or more drugs may be delivered to ocular tissues and/or into the suprachoroidal space via the systems and devices described herein. Delivery of one or more drugs into the suprachoroidal space using the microneedle device described herein may be accomplished by using one or more microneedles. In addition, combinations of one of more drugs may be delivered to the suprachoroidal space using the microneedle device described herein in combination with delivery of one or more drugs via intravitreal (IVT) administration (e.g., intravitreal injection, intravitreal implant or eye drops). Methods of IVT administration are well known in the art. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Cand5, CERE140, Ciganclor, CLT001, CLT003, CLT004, CLT005, complement component 5 aptanier (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimuniab, LFG316, Lucentis, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptame (pegylated), POT4, PRM167, PRS055, QPI1007, ranibizumab, resveratrol, Retilone, retinal pigment epithelium-specific protein 65kDa gene, Retisert, RPE65 derived cone viability factor, RPE65 Gene Therapy, RPGR Gene Therapy, RTP8O1, Sd-rxRNA, serpin peptidase inhibitor Glade F member I gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, volociximab, Votrient, XG102, Xibrom, XV615, and Zybrestat. Accordingly, the methods described herein include administrating via IVT one or more of the drugs listed above in combination with one or more drugs disclosed herein administered into the suprachoroidal space using the microneedle device described herein.

In one embodiment, the drug is formulated for storage and delivery via the microneedle device described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In one embodiment, the fluid drug formulation includes microparticles or nanoparticles, each of which can include at least one drug. Desirably, the microparticles or nanoparticles provide for the controlled release of drug into the ocular tissue. As used herein, the term "microparticle" encompasses microspheres, microcapsules, microparticles, and beads, having a number average diameter of 1 to 100 µm, most preferably 1 to 25 µm. The term "nanoparticles" are particles having a number average diameter of 1 to 1000 nm. Microparticles may or may not be spherical in shape. "Microcapsules" are defined as microparticles having an outer shell surrounding a core of another material. The core can be liquid, gel, solid, gas, or a combination thereof. In one case, the microcapsule may be a "microbubble" having an outer shell surrounding a core of gas, wherein the drug is disposed on the surface of the outer shell, in the outer shell itself, or in the core. Microbubbles may respond to acoustic vibrations as known in the art for diagnosis and/or can be used to burst the microbubble to release its payload afinto a select ocular tissue site. "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharride, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc. which are known in the art to control the kinetics of drug release from particles.

In one embodiment, the fluid drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one that undergoes a phase change upon administration. For instance, a liquid drug formulation may be injected through hollow microneedles into the suprachoroidal space, where it then gels and the drug diffuses out from the gel for controlled release.

While the embodiments and methods herein describe delivering a medicament to a target tissue, the embodiments described herein can be configured to facilitate a biopsy procedure. For example, in some embodiments, a micror3eedie can be inserted into the vitreous of an eye to core a target tissue such as, for example, a tumor. Current biopsy technique includes creation of a sclera flap and suturing the flap, two procedures that put the eye at risk for perforation and tumor seeding. Tumor seeding during fine needle aspiration biopsy of the tumor has been shown to occur experimentally and in clinical practice with commercially available 27-gauge needles and 30-gauge needles and methods currently available. This tumor seeding increases the risk for metastasis and mortality from the tumor. The embodiments described herein overcome this risk by providing a hollow microneedle with a smaller diameter that prohibits cells growing from inside the needle track. Moreover, by adjusting the length of the microneedle a tumor can be cored without the risk of seeding adjacent tissue structures posterior to the tumor.

Although the systems and methods are shown and described herein as providing for delivery of medicaments in the suprachoroidal space, in other embodiments, the systems and the methods described herein can be applicable for delivery of any suitable therapeutic substance to any portion of the eye, such as, the cornea, the retinal area or the vitreous. In other embodiments, any of the systems, methods and devices described herein can be used to deliver any suitable therapeutic substance to any desired target tissue (including non-ocular tissue).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. For example, although the puncture member 320 is described with reference to FIGS. 8-10 as being inserted into ocular tissue prior to the delivery device 300 being moved to the second configuration, in some instances, the delivery device 300 can be moved to the second configuration (FIG. 9) prior to the insertion of the puncture member 320. In some instances, this arrangement can provide for better visualization of the volumetric indicator 346 to ascertain the volume of the drug formulation transferred from the first reservoir 331 to the second reservoir 340.

Where schematics and/or embodiments described above indicate certain components arranged in certain orientations or positions, the arrangement of components may be modified. Similarly, where methods and/or events described above indicate certain events and/or procedures occurring in certain order, the ordering of certain events and/or procedures may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above. For example, although not shown, any of the embodiments described herein can include a safety tab or the like that can be substantially similar in form and/or function as the safety tab 390 included in the delivery device 300 of FIGS. 8-10.

What is claimed:

1. An apparatus, comprising:

a housing;

a cartridge assembly, at least a portion of the cartridge assembly configured to be movably disposed in the housing, the cartridge assembly including a first movable member and a second movable member, the second movable member including a seal member configured to form a fluidic seal with an inner surface of the first movable member, the first movable member defining an inner volume bounded by the seal member and the inner surface of the first movable member, at least a portion of the second movable member being movably disposed in the inner volume between a first position and a second position relative to the first movable member;

a first reservoir disposed within the inner volume such that the first reservoir is disposed in a distal position relative to the second movable member, the first reservoir containing a drug when the second movable member is in its first position relative to the first movable member, the first reservoir not being in fluid communication with the inner volume when the second movable member is in its first position, the first reservoir being placed in fluid communication with the inner volume when the second movable member is in its second position relative to the first movable member, the first movable member including a valve member configured to be transitioned from a closed configuration when the second movable member is in its first position relative to the first movable member to an open configuration (1) when the second movable member is moved toward its second position relative to the first movable member, and (2) in response to an increase in pressure within the first reservoir by distal movement of the second movable member from its first position towards its second position, the valve member further configured to be transitioned from the open configuration to the closed configuration after the second movable member is moved towards its second position relative to the first movable member; and a second reservoir at least partially defined by the housing, a portion of the first movable member being movably disposed in the second reservoir, the second reservoir being fluidically isolated from the inner volume when the second movable member is in its first position relative to the first movable member and the valve member is in its closed configuration, the second reservoir being placed in fluid communication with the inner volume when the second movable member is moved toward its second position relative to the first movable member to receive a volume of the drug from the first reservoir and the valve member is in its open configuration, the first movable member and the second movable member collectively configured to be moved distally from a first position relative to the housing to a second position relative to the housing to expel the volume of the drug from the second reservoir.

2. The apparatus of claim 1, wherein the housing has a proximal end portion and a distal end portion, the proximal end portion defining an opening to receive at least a portion of the cartridge assembly, the distal end portion being physically and fluidically coupled to a puncture member, the puncture member being in fluid communication with the second reservoir.

3. The apparatus of claim 2, wherein the puncture member is configured to puncture ocular tissue of a patient.

4. The apparatus of claim 1, wherein the second reservoir includes a volumetric indicator.

5. The apparatus of claim 1, wherein the first reservoir is a deformable reservoir, the first reservoir including a portion configured to break open when the second movable member is moved toward its second position relative to the first movable member.

6. The apparatus of claim 1, wherein the first reservoir is a deformable reservoir, the first reservoir configured to be transitioned from a substantially undeformed configuration, in which the first reservoir contains the drug, to a deformed configuration, in which the volume of the drug is disposed substantially outside of the first reservoir.

7. The apparatus of claim 6, wherein the first movable member includes an inner surface that forms a shoulder configured to be in contact with the first reservoir, the shoulder configured to transition the first reservoir, at a point of the contact, from the substantially undeformed configuration to the deformed configuration in response to the movement of the second movable member from its first position to its second position relative to the first movable member.

8. The apparatus of claim 1, further comprising:
a safety tab movably coupled to the housing, the safety tab configured to be placed in contact with first movable member to selectively limit a movement of the first movable member relative to the housing.

9. The apparatus of claim 1, wherein the valve member is a check valve, a ball valve, a diaphragm valve, a stop valve, or a duckbill valve.

10. The apparatus of claim 1, wherein the valve member is a one way valve.

11. The apparatus of claim 1, further comprising:
an actuator configured to transition the valve between its closed configuration and its open configuration, the actuator including at least one of a toggle, a switch, a button, a slide, or a knob.

12. The apparatus of claim 1, wherein the valve member is a first valve member, the housing including a second valve member disposed in the second reservoir.

13. The apparatus of claim 1, wherein the inner volume is a first inner volume and the housing defines a second inner volume and is configured to receive a portion of a safety tab such that the safety tab extends from a first radial side of the housing to a second radial side of the housing, traversing the second inner volume, the first radial side being located opposite the second radial side, and engages the first movable member to selectively limit movement of the first movable member relative to the housing when the safety tab is engaged with the first movable member and the housing.

14. The apparatus of claim 1, wherein the valve member is a first valve member, the second reservoir further including a second valve member, the second valve member configured to be transitioned from a closed configuration to an open configuration in response to the first movable member being moved distally from the first position relative to the housing to the second position relative to the housing.

15. The apparatus of claim 1, wherein the housing has a proximal end portion and a distal end portion, the proximal end portion defining an opening to receive at least a portion of the cartridge assembly, the distal end portion being physically and fluidically coupled to a puncture member, the puncture member configured to be in fluid communication with the second reservoir in response to an increase in pressure in the second reservoir.

16. An apparatus, comprising:
a housing having a distal end portion, the distal end portion defining a substantially rigid reservoir physically and fluidically coupled to a puncture member, the puncture member configured to puncture ocular tissue of a patient; and a cartridge assembly configured to be movably disposed in the housing, the cartridge assembly including a first movable member and a second movable member, at least a portion of the first movable member configured to be disposed in the substantially rigid reservoir, the first movable member having a shoulder and defining an inner volume, at least a portion of the second movable member being movably disposed in the inner volume between a first position and a second position, the cartridge assembly including a deformable reservoir disposed within the inner volume between the shoulder and the second movable member, the shoulder having an inner surface including a protrusion configured to pierce the deformable reservoir when the second movable member is moved relative to the first movable member from its first position to its second position to transition the deformable reservoir from a first configuration, in which a drug is contained within the deformable reservoir, to a second configuration, in which a volume of the drug is disposed substantially outside the deformable reservoir, the substantially rigid reservoir being fluidically isolated from the inner volume when the second movable member is in its first position, the substantially rigid reservoir configured to receive the volume of the drug from the inner volume when the second movable member is moved relative to the first movable member toward its second position, the first movable member of the cartridge assembly being movable relative to the housing from a first position to a second position to deliver the volume of the drug, via the puncture member, from the second reservoir to the ocular tissue, the shoulder further having an outer surface configured to contact a safety tab when the safety tab is movably coupled to the housing, the contact with the safety tab further configured to selectively limit movement of the first movable member relative to the housing.

17. The apparatus of claim 16, wherein the puncture member defines a lumen in fluid communication with the substantially rigid reservoir, the first movable member of the cartridge assembly configured to move relative to the housing from its first position to its second position such that a pressure within the substantially rigid reservoir is sufficient to urge a flow of the drug through the lumen.

18. The apparatus of claim 16, wherein the puncture member has a proximal end portion and a distal end portion, the proximal end portion being physically and fluidically coupled to the substantially rigid reservoir, the distal end portion forming a beveled edge, the beveled edge configured to pierce ocular tissue while minimizing deformation at or near a pierce site.

19. The apparatus of claim 16, wherein the second movable member is configured to move relative to the first movable member from its first position toward its second position in response to an applied force such that a pressure within the inner volume is increased from a first pressure to a second pressure, the second pressure being sufficient to transition the deformable reservoir from the its first configuration to its second configuration.

20. The apparatus of claim 19, wherein the first movable member includes a valve member, the valve member configured to be in a closed configuration when a pressure within the inner volume is less than the second pressure, the valve member configured to transition from the closed configuration to the open configuration when a pressure within the inner volume is substantially equal to the second pressure.

21. The apparatus of claim 16, wherein the shoulder includes at least one protrusion, the protrusion having a barbed surface configured to puncture the deformable reservoir to place the deformable reservoir in its second configuration.

22. The apparatus of claim 16, wherein:
the first movable member and the second movable member are configured to be moved in a same direction relative to the housing to deliver the volume of the drug.

23. An apparatus, comprising:
a housing defining a first inner volume configured to receive a safety tab, a distal end portion of the housing being physically and fluidically coupled to a puncture member configured to puncture ocular tissue;
a first movable member defining a second inner volume and movably disposed in the first inner volume of the housing, the safety tab configured to extend from a first radial side of the housing to a second radial side of the housing, traversing a portion of the first inner volume of the housing, when releasably coupled to the housing to engage the first movable member to selectively limit movement of the first movable member relative to the housing, the first radial side being located opposite the second radial side;
a second movable member at least partially disposed in the second inner volume of the first movable member and being movable relative to the first movable member between a first position and a second position;
a first reservoir disposed within the second inner volume of the first movable member, the first reservoir configured to be transitioned between a first configuration, in which the first reservoir contains a drug, and a second configuration, in which a volume of the drug is disposed within the second inner volume of the first movable member and substantially outside of the first reservoir, when the second movable member is moved from its first position to its second position, respectively; and
a second reservoir at least partially defined by the housing, a portion of the first movable member being movably disposed in the second reservoir, the second reservoir being fluidically isolated from the second inner volume of the first movable member when the second movable member is in its first position, the second reservoir being placed in fluid communication with the second inner volume of the first movable member to receive the volume of the drug when the second movable member is moved toward its second position, the first movable member configured to be disengaged from the safety tab and moved within the second reservoir from a first position to a second position to deliver the volume of the drug, via the puncture member, from the second reservoir to the ocular tissue.

24. The apparatus of claim 23, wherein the safety tab is removably coupled to the housing, the safety tab configured to be removed from the housing when the second movable member is placed in its second position relative to the first movable member.

25. The apparatus of claim 23, wherein the second reservoir includes a volumetric indicator, the second position of the second movable member being associated with the second reservoir receiving a predetermined volume of the drug, the predetermined volume of the drug being determined based at least in part on the volumetric indicator.

26. The apparatus of claim 23, wherein the second movable member is configured to be moved substantially concurrently with the first movable member, relative to the housing, to deliver the volume of the drug from the second reservoir.

27. The apparatus of claim 23, wherein first reservoir is a deformable pouch, the first movable member including an inner surface configured to puncture a portion of the first reservoir to transition the first reservoir from its first configuration to its second configuration.

28. The apparatus of claim 23, wherein:
the first inner volume of the housing defines a slot configured to receive the safety tab.

29. The apparatus of claim 23, wherein:
the safety tab is configured to be disposed between the distal end portion of the housing and a proximal end portion of the housing when the safety tab is engaged with the first movable member.

30. The apparatus of claim 23, wherein the first movable member is partially disposed within the first inner volume when the safety tab is releasably coupled to the housing to selectively limit movement of the first movable member relative to the housing.

* * * * *